(12) United States Patent
Schwartz et al.

(10) Patent No.: US 7,546,048 B2
(45) Date of Patent: Jun. 9, 2009

(54) METHOD FOR DETERMINING INK USAGE EFFICIENCY IN COMMERCIAL PRINTING PROCESSES USING PIGMENTS AND QUANTITATIVE TESTS

(75) Inventors: Russell J. Schwartz, Cincinnati, OH (US); Constantinos Nicolaou, Cincinnati, OH (US); Xin Zhang, Mason, OH (US); Donald C. Henderson, Loveland, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 425 days.

(21) Appl. No.: 11/332,668

(22) Filed: Jan. 12, 2006

(65) Prior Publication Data
US 2007/0161115 A1 Jul. 12, 2007

(51) Int. Cl.
G03G 15/10 (2006.01)
G01N 21/00 (2006.01)
(52) U.S. Cl. .............................. 399/60; 399/30; 399/49; 399/64; 399/57; 347/100; 347/19; 347/7
(58) Field of Classification Search ................. 399/270, 399/30, 27; 101/170, 211, 484, 491; 347/100
See application file for complete search history.

(56) References Cited

U.S. PATENT DOCUMENTS

| 3,436,648 | A | * | 4/1969 | Kim | ........................... | 324/453 |
| 3,821,938 | A | * | 7/1974 | Bacon et al. | .................. | 399/30 |
| 5,204,699 | A | * | 4/1993 | Birnbaum et al. | ........... | 347/131 |
| 5,517,913 | A | * | 5/1996 | Oshio et al. | ................. | 101/119 |
| RE35,911 | E | * | 9/1998 | Seitz et al. | ................. | 358/3.29 |
| 6,671,050 | B2 | * | 12/2003 | Sugiyama et al. | ........... | 356/405 |

OTHER PUBLICATIONS

Hitomi Hamada et al., An Application of the X-ray Fluorescence Method to Quantification of Ink Printed on Paper Surfaces (Part 2) Analysis of Ink Mottling, Pulp and Paper Research Conference, Tokyo, Japan, Jun. 18-19, 2001, pp. 152-155.

* cited by examiner

Primary Examiner—Andrew H. Hirshfeld
Assistant Examiner—John Zhu
(74) Attorney, Agent, or Firm—Kramer Levin Naftalis & Frankel LLP

(57) ABSTRACT

A method for determining printing ink usage efficiency (weight of ink required to print a given area) in a printing process is disclosed where the method is based on the analysis of pigment in the printed ink.

20 Claims, 20 Drawing Sheets

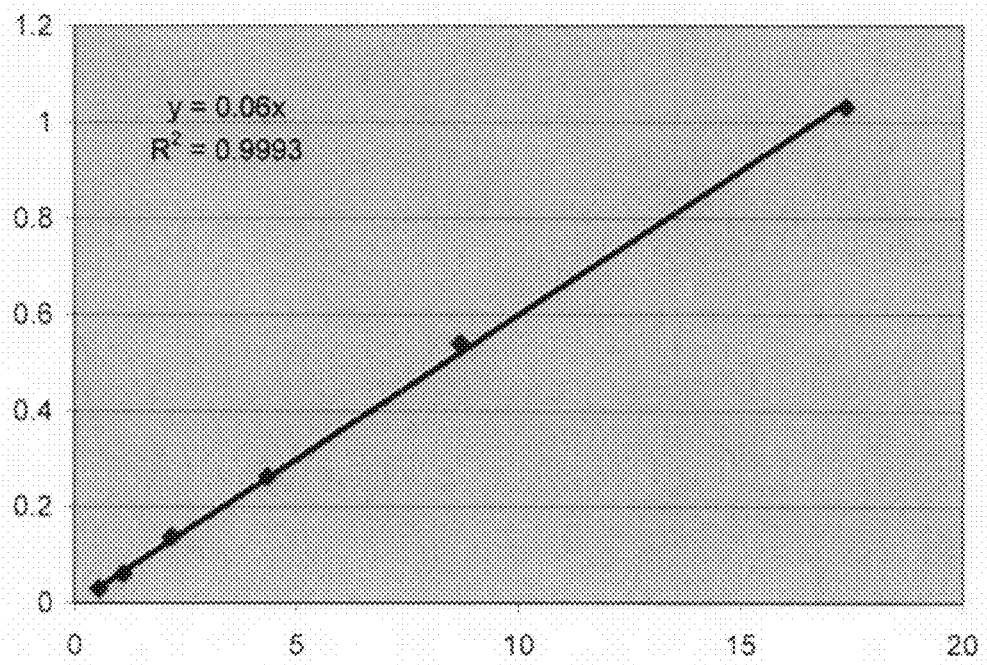

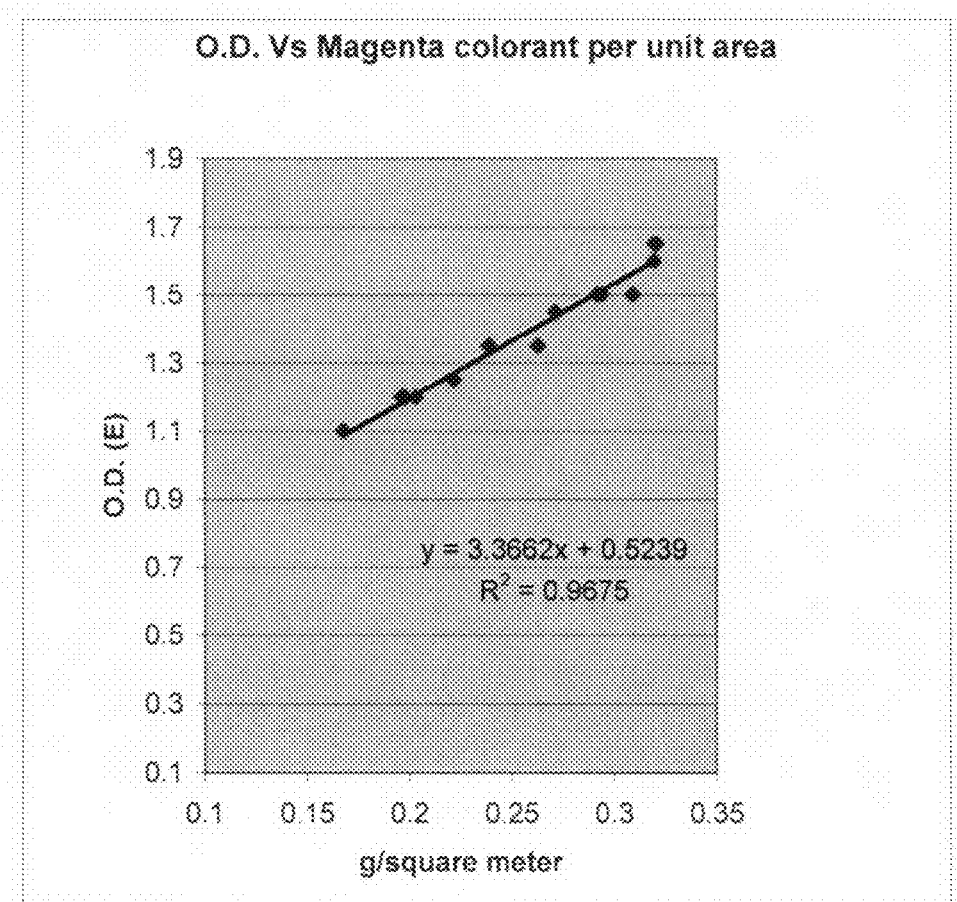

METHOD FOR DETERMINING INK USAGE EFFICIENCY IN COMMERCIAL PRINTING PROCESSES USING PIGMENTS AND QUANTITATIVE TESTS

FIELD OF THE INVENTION

The invention relates to a method for determining ink usage efficiency in commercial printing processes comprising the use of pigments and quantitative test methods based on solvent extraction, filtration and UV-Visible spectrophotometry.

BACKGROUND OF THE INVENTION

To reproduce a color original, an electronic color scanner is used to separate the image into its cyan, magenta and yellow components using red, green and blue filters. A combination of these is then used to create the black component. The output of the scanner consists of a halftone screen for each of the four colors of the original with graduated dot sizes reproducing the tonal range of the original. Printing plates are then made from these screens which are then used to print the image on paper using the four process inks.

Predictable and consistent color is of paramount importance to printers. To ensure color control and to maintain a consistent printed product, the ink film thickness and the size and color strength of these halftone dots must be monitored and controlled.

The inks used are for the most part transparent, and act as color filters. When white light is shining on a green ink on white paper it is seen as green since the blue and red parts of the spectrum are absorbed as the light passes through the ink. The transmitted light is reflected by the white paper and is filtered a second time as it reemerges from the ink surface (see FIG. 1). The thicker the ink film, the more light the ink absorbs and the darker the ink seems. Thus, a thick ink appears to have a greater density.

In the halftone process the tonal scale of the image is represented with dots of differing sizes. The assumption is that the ink film thickness of each dot is the same irrespective of its size or diameter. Since it is difficult to separate the individual components that create the image, in order to measure the ink film thickness and to ensure its uniformity across the press sheet, a series of control test strips of solid ink, i.e. 100% dot, for each color are placed in the color bar and are measured with the reflection densitometer.

These test strips as shown in FIG. 2, called print control strips or color bars, are available commercially from various vendors, and consist of strips of film containing the various test elements for each of the four colors. In some cases six color versions are available when special colors might be used. The usual densitometric targets in a colorbar are: Solid Ink Density, Dot Area/Gain half and three-quarter tints, Contrast and the Trapping of ink overprints.

The densitometer emits white light (approximately equal amount of red, green and blue) which is focused onto the printed surface and collects light reflected from the print. The densitometer subtracts the amount of light returned from the amount of light shone to determine how much was absorbed. The reflected light is received by a photo diode and then converted into an electrical signal. The electrical current is compared to a reference value (from white light) and the difference is used to calculate the film reflectance and hence the optical density.

In the United States, it has been the custom to use Status T (wide band) filters, while in Europe Status E filters are used. Therefore in order to compare O.D. results, the same type of calibrated filter must be used. The filters used to read process colors are red for cyan ink, green for magenta ink, and blue for yellow ink. Typical status T O.D. values for solid ink density are 0.90 to 1.10 for yellow, 1.10 to 1.40 for magenta, 1.25-1.45 for cyan and 1.55 to 1.85 for black.

The densitometer within certain limitations, gives higher density readings with increasing ink film thickness. When the ink film thickness approaches a certain point, however, there is no further increase in density and any extra ink added is wasted.

Ink usage efficiency, most often referred to as ink mileage, and its press performance are very important criteria for assessing the value of inks. Press mileage is usually expressed as lbs or Kg of ink required to print 1000 prints at a given SWOP Optical Density (O.D). In order to obtain accurate ink mileage on the press the printers have to measure the amount of ink used to print at least 500,000 prints, preferably 1,000,000 prints. This method is time consuming, has poor precision due to lack of repeatability, which would be very costly to determine, and press trials are expensive. Press mileage could vary significantly due to variation in color saturation of the prints which can differ by as much as 10% within a given SWOP range. Improper start up procedures, changes in ink/water balance, or changes in ink tack and body can cause excessive waste of paper and print density variation and thus decrease the accuracy of press mileage.

It is important to note that the densitometer readings are on a logarithmic scale. A density of zero indicates that 100% of the incident light is being reflected. At a density of 1.00 only 10% of the light is being reflected, and at a density of 2.00 only 1% of the light is being reflected. The O.D may be defined as follows:

$$O.D. = \log\left(\frac{100}{\%R}\right)$$

where R is the reflectance.

High print densities can lead to poorer ink mileage due to non linearity between the weight of ink film and light absorption by the colorant. Densitometers also have difficulty in measuring accurately very light spot colors (low O.D.).

The arrangement of the components of a typical reflection densitometer is illustrated in FIG. 3.

Hamada et al. (Pulp and Paper Research Conference, Tokkyo, Japan, 18-19 Jun. 2001, pp 152-155, Japan TAPPI) discloses that the amount of printed cyan ink can be determined by measuring copper intensity using X-ray fluorescence. Specifically, Hamada et al. discloses that the content of copper present in a cyan ink printed on paper can be mesured as an intensity of the peak in the X-ray fluorescence spectrum. However, it is difficult to use this method to quantitate small amounts of printed ink (less than 1 g of ink/1 $m^2$ of printed paper). In addition, calculating printing ink efficiency using this method is not practical or cost efficient and is only limited to inks with copper additives such as cyan ink which contains copper-phthalocyanine as the blue pigment.

In view of the foregoing, it is therefore desirable to provide analytical methods for measuring ink usage efficiency (ink mileage) in commercial printing processes accurately, faster and at lower cost, based on spectrophotometric principles whereby the total chromophore content of the taggant per unit area of print as well as the colorant content of the ink used in the print is measured. The method can be applied to all types of printing inks including heatset, UV flexo and publication gravure. The ink mileage test method of the present invention can be used as quality control tool to accurately predict press mileage, for the development of improved inks and colorants at a faster rate to increase the speed of new products to market and to predict more accurately the cost of printing. The cost to print is defined as dollars needed to print 1000 square meters of print at mid SWOP O.D.

Cost of print=$/1000 $m^2$

SUMMARY OF THE INVENTION

The present invention provides a method for determining printing ink usage efficiency (weight of ink required to print a given area) in a printing process based on an analysis of pigment in a printed ink, said method comprising:
 (a) extracting said printed ink containing said pigment from a printed surface area into a liquid solution;
 (b) measuring amount of said pigment in the extracted ink; and
 (c) calculating said printing ink usage efficiency based on the analysis of and the amount of pigment in said area.

The present invention also provides a method for determining printing ink usage efficiency (weight of ink required to print a given area) in a printing process based on the analysis of pigment in said printed ink, said method comprising:
 (a) extracting ink containing said pigment from a printed surface area into a liquid solution and placing said solution in a container transparent to UV-Visible light;
 (b) measuring absorbance amount of said pigment in extracted ink by UV-Visible spectrophotometry at a specific wavelength; and
 (c) calculating concentration of said pigment using the following equation:

$c=A/a_\lambda b$ where A is the measured absorbance, $a_\lambda$ is an absorptivity coefficient of said pigment and is dependent on said wavelength, b is the path length of said container, and c is the pigment concentration in said liquid solution;
 (d) calculating absolute amount of said pigment in said liquid solution; and
 (e) calculating said printing ink usage efficiency based on the printed surface area and amount of pigment in said area.

The present invention further provides a product comprising printed ink, wherein the printing ink usage efficiency of said ink was determined according to the method of the present invention.

Other objects and advantages of the present invention will become apparent from the following description and appended claims.

BRIEF DESCRIPTION OF THE DRAWINGS

FIG. 7A shows a calibration curve (absorbance [x axix] v. mg/L [y axis]) for magenta colorant.

FIG. 10 shows a Plot of Colorant per area Vs O.D. of magenta prints.ectra of Std Yellow colorant 0.28 mg/L to 9.26 mg/L.

DETAILED DESCRIPTION OF THE INVENTION

Figure 1:
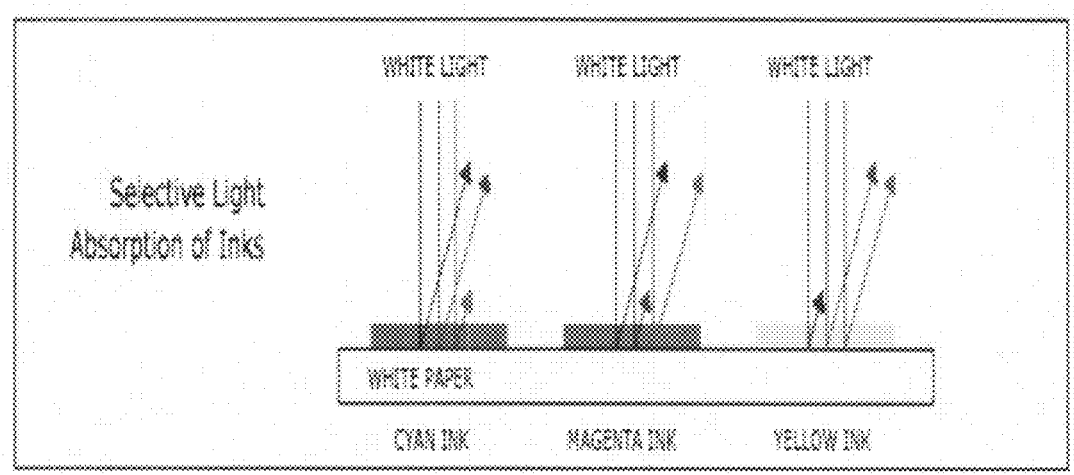
FIG. 1 shows selective light absorption of cyan, magenta and yellow inks.
Figure 2:
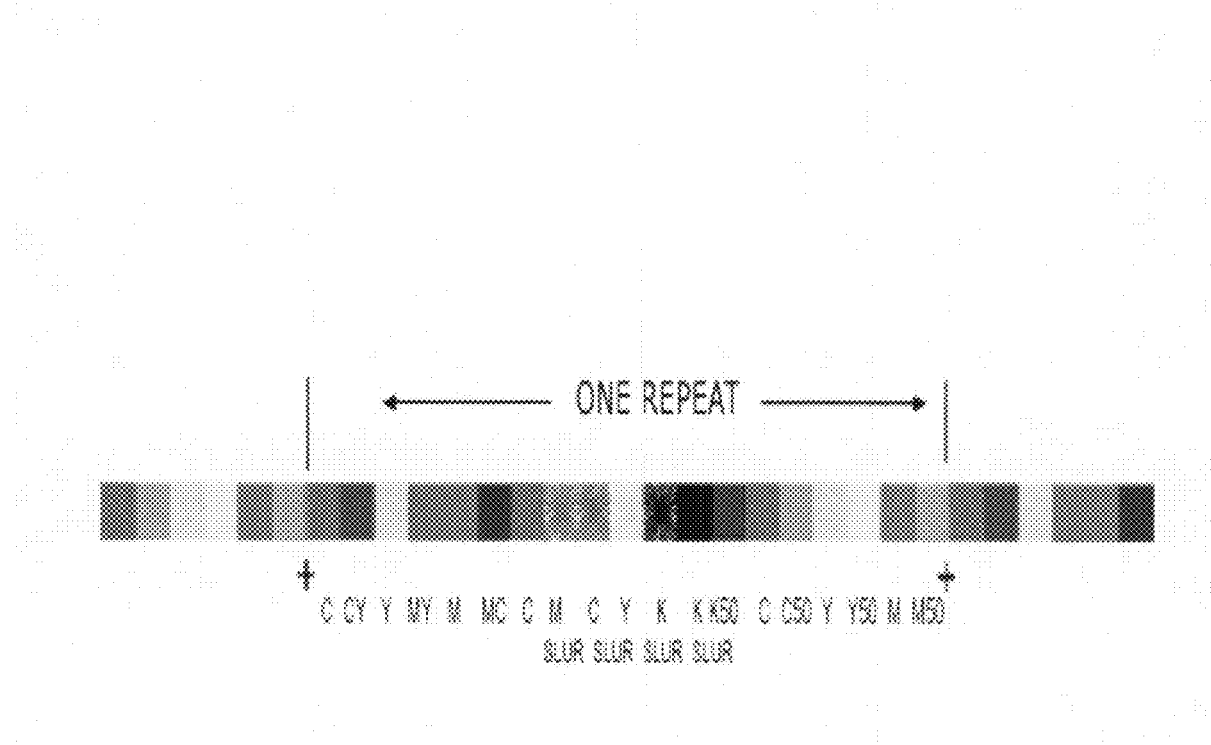
FIG. 2 shows a control test strip of solid ink, containing the various test elements for each of the four colors.
Figure 3:
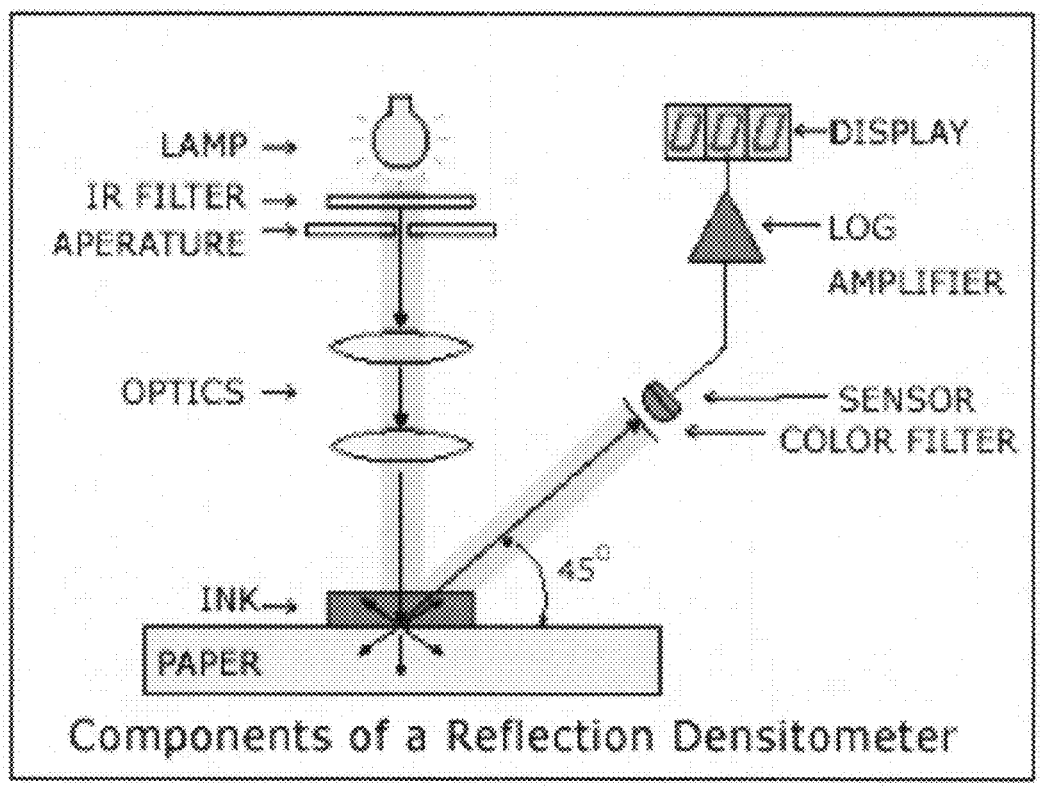
FIG. 3 shows the arrangement of the components of a typical reflection densitometer.

The principle of the ink mileage method of the present invention is based on measuring the amount of colored pigments per unit area of print at a given O.D and the amount of the colored pigments in the ink used to make the print. This is accomplished by removing the ink from the printed surface, dissolving the colorants in appropriate solvents, filtering and then measuring the amount of pigment. Preferably, the pigment absorbs visible light and the amount of colorant or pigment in the solution is calculated in accordance to Beer's law of light absorption by dilute solutions.

Preferably, the pigment is selected from the group consisting of azo and phthalocyanine pigments.

Also, preferably, the ink is selected from the group consisting of publication inks and packaging inks. More preferably, the ink is selected from the group consisting of gravure inks, flexo inks and offset inks.

Again preferably, the printed surface is on a color bar or registration mark. Also preferably, the ink is extracted from a printed area that measures from about 2 $mm^2$ to about 1575 $mm^2$ by a liquid solution or is dissolved into a liquid solution that is preferebly filtered prior to measurement of the aborbance amount of the pigment.

Also preferably, the liquid solution used to extract said printing ink is selected from the group consisting of ortho-dichlorobenzene, 1-methylnaphthalene and acidified aqueous ethanol. When the pigment is an azo, phthalocyanine, or an azo yellow pigment, then the liquid solution used to extract it is ortho-dichlorobenzene, 1-methylnaphthalene or acidified aqueous ethanol, respectively.

It is preferable that the reflectance color saturation is measured for said printed area prior to the extraction of the ink in the present invention. This measurement can be done with any mathematical function or light filter that acts to modify and quantify particular reflected wavelengths of visual light so that a specific color can be quantified for depth or saturation of color. Reflectance color saturation measures include optical density, any K/S functions, depth of shade methods, or chromatic methods.

It is more preferable that the Optical Density is measured for said printed area prior to the extraction of the ink in the present invention. This way and as indicated above, the ink usage efficiency is expressed as ink usage efficienct at measured Optical Density.

The present invention also provides a method for determining ink usage efficiency at a at SWOP density (Specifications for Web Offset Publications density) comprising: (a) determining ink usage efficiency at measured Optical Density; and (b) determining ink usage efficiency at SWOP density according to the following formula:

ink usage efficiency at SWOP density (amount of ink/ printed area at SWOP )=(ink usage efficiency at measured Optical Density)·(C.F.)

wherein C.F. is a correction factor to adjust for variation in taggant saturation within a given SWOP Optical Density range.

Ink usage efficiency (Ink mileage) is primarily dependant on the total chromophore content of the ink, on the particle size distribution of the colorants and ink film thickness. At constant chromophore content the ink mileage decreases as the particle size increases. Thus measurement of unit weight of colorant per unit print area of print at SWOP O.D. provides the efficiency of light absorption by the colorant. Within certain limits (and always within Beer's law) the amount of light absorption increases with increasing colorant content. With a higher colorant content ink a thinner film is required in order to maintain constant SWOP O.D. Printing thinner films can reduce cost (less binder), increase ink usage efficiency and help to minimize dot gain, misting and rub off problems.

The ink usage efficiency can be calculated from the O.D. of the print, the amount of colored taggant per unit area of the print and the amount of colored taggant in the ink used to make the print. A correction factor (CF) is applied to account for variation in color saturation while printing at a given SWOP O.D. This arises because the target optical density is usually the mid-point of the SWOP range for a given paper substrate. Prints are rarely at the exact same color saturation during the printing process and can differ by more than 10% within a given SWOP O.D. Therefore, to improve the accuracy of the ink mileage results, the mileage values must be corrected to a constant color saturation level. For example, it would be incorrect to claim that an ink gives 10% better mileage if the prints of the claimed stronger ink were printed at a 10% lower color saturation level. This is because the Optical Density is not a linear function of color strength. For example, if the yellow status T optical density is raised on a no ink penetration stock, such as Leneta card, from 0.90 to 1.00 the actual color strength increase as measured by Tristimulus is 28%, not 10% as would be predicted by the optical density values. Ink usage efficiency or Ink mileage, can be calculated according to the following equation.

ink usage efficiency=(m$^2$/kg ink at "$x$" O.D.)(C.F.)
=m$^2$/kg ink at SWOP O.D.

wherein, O.D. is the Optical Density, C.F. is a correction factor to adjust for variation in color saturation within a given SWOP O.D range and SWOP stands for Specifications for Web Offset Publications.

The calculated Ink usage efficiency value is compared to press mileage results to assess the applicability of the Ink usage efficiency for predicting press mileage.

The colored taggant absorption efficiency is calculated in terms of print area per weight of colorant (m$^2$/g) at a given O.D. according to the equation colorant efficiency=m$^2$/g taggant at "$x$"O.D.

This requires only the identification of the colored taggant(s) and the amount of colored taggant per unit print area. The colored taggant absorption efficiency can be used to compare the absorption efficiency of commercial prints for which there is no available ink sample, to the efficiency of known prints for the purpose evaluating competitive prints.

In addition, the methods of this invention are used to calculate the relative ink mileage efficiency by normalizing the results against a control or a reference ink sample.

In order to measure the amount of a specific colored taggant in a print or ink, pure compounds of each colored taggant are used to determine the absorptivity coefficient (defined as absorbance·liter·mg$^{-1}$) of each taggant at the wavelength of maximum absorption. The absorptivity coefficient depends on the specific chromophore and the solvent in which it is dissolved. Different solvents can be used in order to achieve complete dissolution of the colored taggant in question and obtain the total chromophore content.

Prints disclosed hereinbelow were prepared using a Prufbau printability tester and an X-Rite 938 spectrodensitometer. Prints were reproducible to ±0.03 Optical Density units. Some prints were printed on commercial presses.

Print signatures made from inks were cut into square pieces measuring 0.8789 square inches (567 mm$^2$=5.67×10$^{-4}$ m$^2$) or 2.4414 square inches (1575 mm$^2$=15.75×10$^{-4}$ m$^2$) using a punch type cutting tool (McGill® Craftivity™, StrongArm with McGill Stacking Squares). The area was confirmed using a digital caliper (Brown & Sharp Digit-Cal MK IV model 599-571-4) accurate to 0.01 mm.

The area of individual color bars strips on commercial prints was measured using the digital caliper tool while observing under a light microscope at 10× magnification. The print areas used in the present invention method varied from 2 mm$^2$ to 1575 mm$^2$.

The O.D. of the cut prints was measured several times (typically 4-10 measurements were taken) in order to obtain a representative density value for each print.

The colored taggants in the prints were dissolved in appropriate solvents and the colorant amount in Kg/m$^2$ was measured by visible spectrophotomtery based on Beer's law.

Beer's law (also called the Beer-Lambert-Bouguer law or Beer-Lambert law) was used to measure the amount absorbing taggant in the print. Beer's law is the linear relationship between absorbance and concentration of an absorber of electromagnetic radiation. The general Beer's law is usually written as:

A=a$_\lambda$ b c where A is the measured absorbance, a$_\lambda$ is a wavelength-dependent absorptivity coefficient, b is the path length(cm), and c is the analyte concentration (mg/liter). The absorptivity coefficient a$_\lambda$ may be expressed as Liters mg$^{-1}$ cm$^{-1}$.

If multiple species that absorb light at a given wavelength are present in a sample, the total absorbance at that wavelength is the sum due to all the absorbers:

$$A=(a_1bc_1)+(a_2bc_2)+a_3bc_3)+\ldots$$

where the subscripts refer to the absorptivity and concentration of the different absorbing species that are present.

Experimental measurements are usually made in terms of transmittance (T), which is defined as:

$$T = \frac{P}{P_0}$$

where P is the power of light after it passes through the sample and $P_o$ is the initial light power. The relation between A and T is:

$$A = -\log(T) = -\log\left(\frac{P}{P_0}\right)$$

Figure 4:
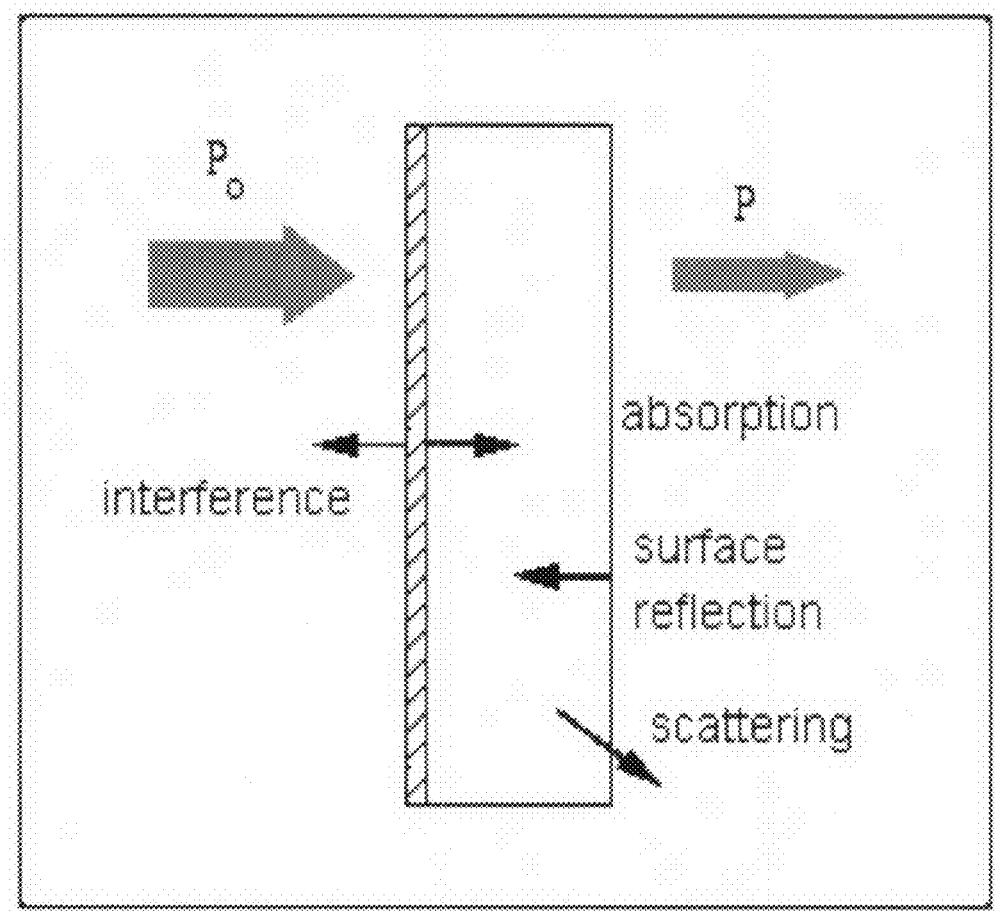
FIG. 4 shows absorption of light through an optical filter and includes other processes that decreases the transmittance such as surface reflectance and scattering.

FIG. 4 shows the case of absorption of light through an optical filter and includes other processes that decreases the transmittance such as surface reflectance and scattering.

Figure 5:
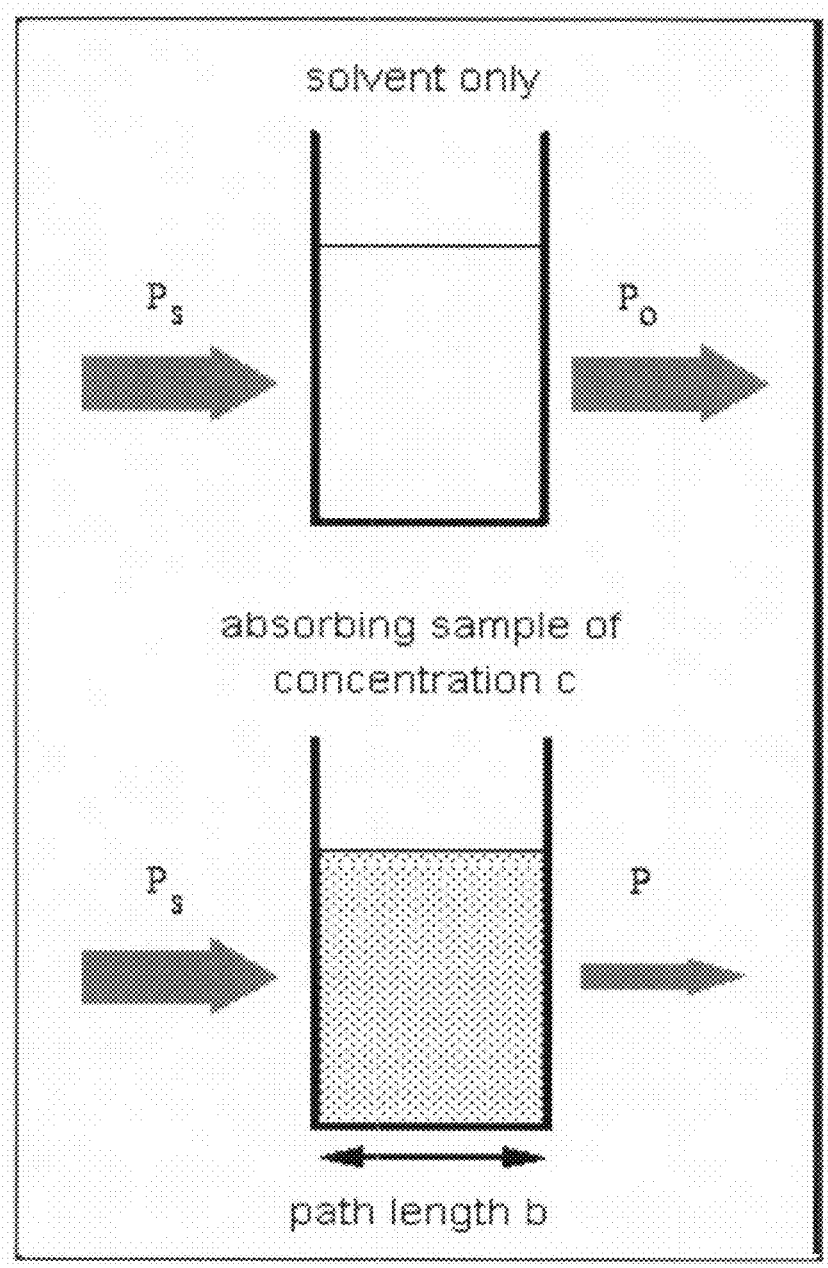
FIG. 5 shows the two transmittance measurements that are necessary to use absorption to determine the concentration of an analyte in solution. The top diagram is for solvent only and the bottom is for an absorbing sample in the same solvent.

In analytical applications, one wants to measure the concentration of an analyte independent of the effects of reflection, solvent absorption, or other interferences. FIG. 5 shows the two transmittance measurements that are necessary to use absorption to determine the concentration of an analyte in solution. The top diagram is for solvent only and the bottom is for an absorbing sample in the same solvent. In this example, $P_S$ is the source light power that is incident on a sample, P is the measured light power after passing through the analyte, solvent, and sample holder, and $P_o$ is the measured light power after passing through only the solvent and sample holder. The measured transmittance in this case is attributed to the analyte.

In the present invention the Perkin Elmer Lambda 40 UV-Visible spectrophotometer was used in the absorbance mode for all measurements used and spectra were recorded in the 350 nm to 850 nm range.

The unknown concentration of an analyte can be determined by measuring the amount of light that a sample solution absorbs and applying Beer's law. If the absorptivity coefficient is not known, the unknown concentration can be determined using a working curve of absorbance versus concentration derived from standards.

Figure 6:
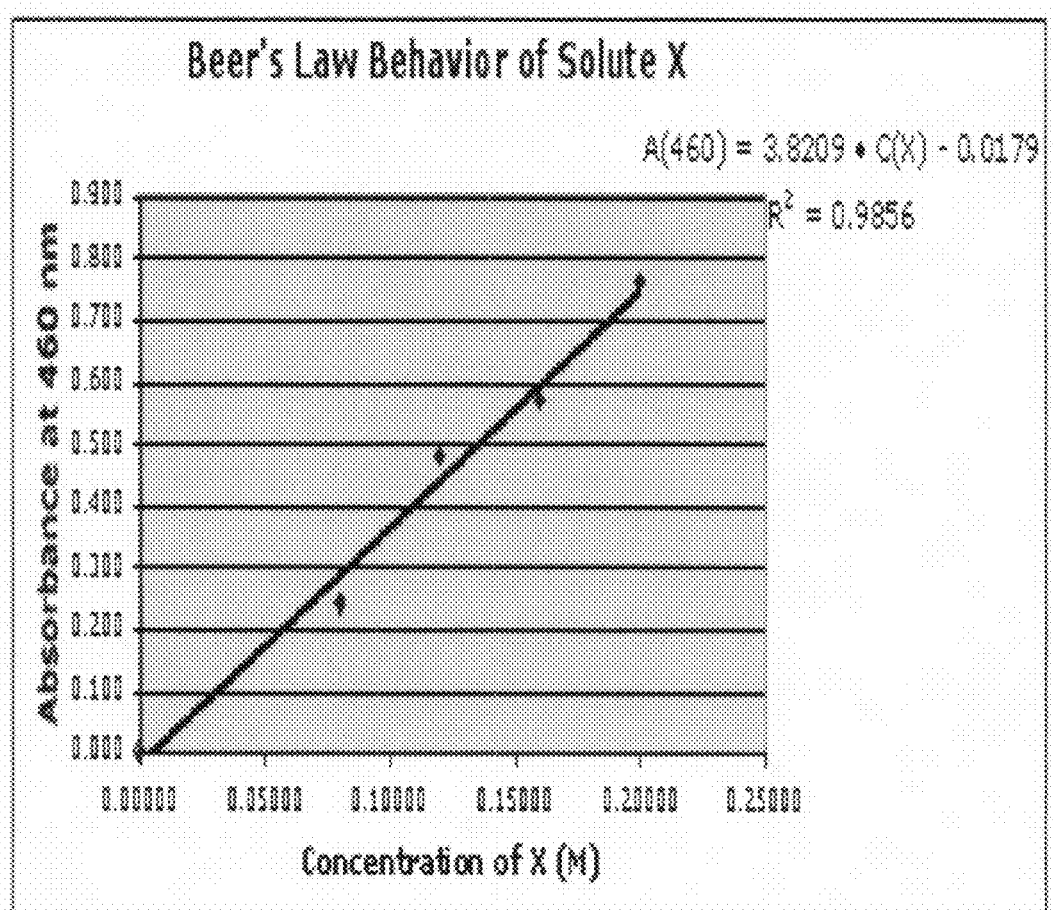
FIG. 6 shows a working curve which is a plot of the analytical signal (the instrument or detector response) as a function of analyte X concentration.

A working curve is a plot of the analytical signal (the instrument or detector response) as a function of analyte concentration. These working curves are obtained by measuring the signal from a series of standards of known concentration. The working curves are then used to determine the concentration of an unknown sample, or to calibrate the linearity of an analytical instrument. An example of a working curve is illustrated in FIG. 6

The linear regression equation of the calibration line, y=mx+b, is used to calculated the concentration of the analyte in the sample solution.

$$x = \left(\frac{y-b}{m}\right)$$

where x=concentration of the sample mg/L or Moles/L y=absorbance of the sample solution m=slope b=intercept In the methods of the present invention, the intercept is zero and the equation becomes $$x = \left(\frac{y}{m}\right)$$

This equation was used to determine the absorptivity coefficient of the dissolved colored taggants from the prints and inks, in dilute solutions.

The spectrophotometer is calibrated monthly according to the manufacturers recommendations using ISO 9001 procedures and NIST standards. The spectrophotometer is balanced just prior to analysis by scanning solvent only in both the reference cell and the sample cell.

Absorptivity Coefficient of Magenta Colored Pigment

For the determination of the absorptivity coefficient of the Magenta colored taggant, 3.000±0.2 mg, were weighed on a microbalance, accurate to 0.1 mg, and the colorant was dissolved in 250 ml of acidified alcohol (125 ml ethanol, 120 ml water, 5 ml concentrated $H_2SO_4$). The absorbance of the resulting solution was measured on the Perkin Elmer Lambda 40 UV-Visible spectrophotometer between 400 nm-700 nm.

The sample cell is filled with the Magenta colorant solution and then placed in the sample port position and a spectrophotometric curve is scanned. The absorbance (A) at the wavelength of maximum absorption is recorded and the absorptivity coefficient is calculated as $$a_\lambda = \left(\frac{A}{c}\right)$$

The absorbance of pure Magenta colorant at c=12.492 mg/Liter is 0.7495, hence the absorptivity coefficient is $$a_\lambda=0.7495/12.492=0.0600 \text{ liter}\cdot\text{mg}^{-1}\cdot\text{cm}^{-1}.$$

Figure 7B:
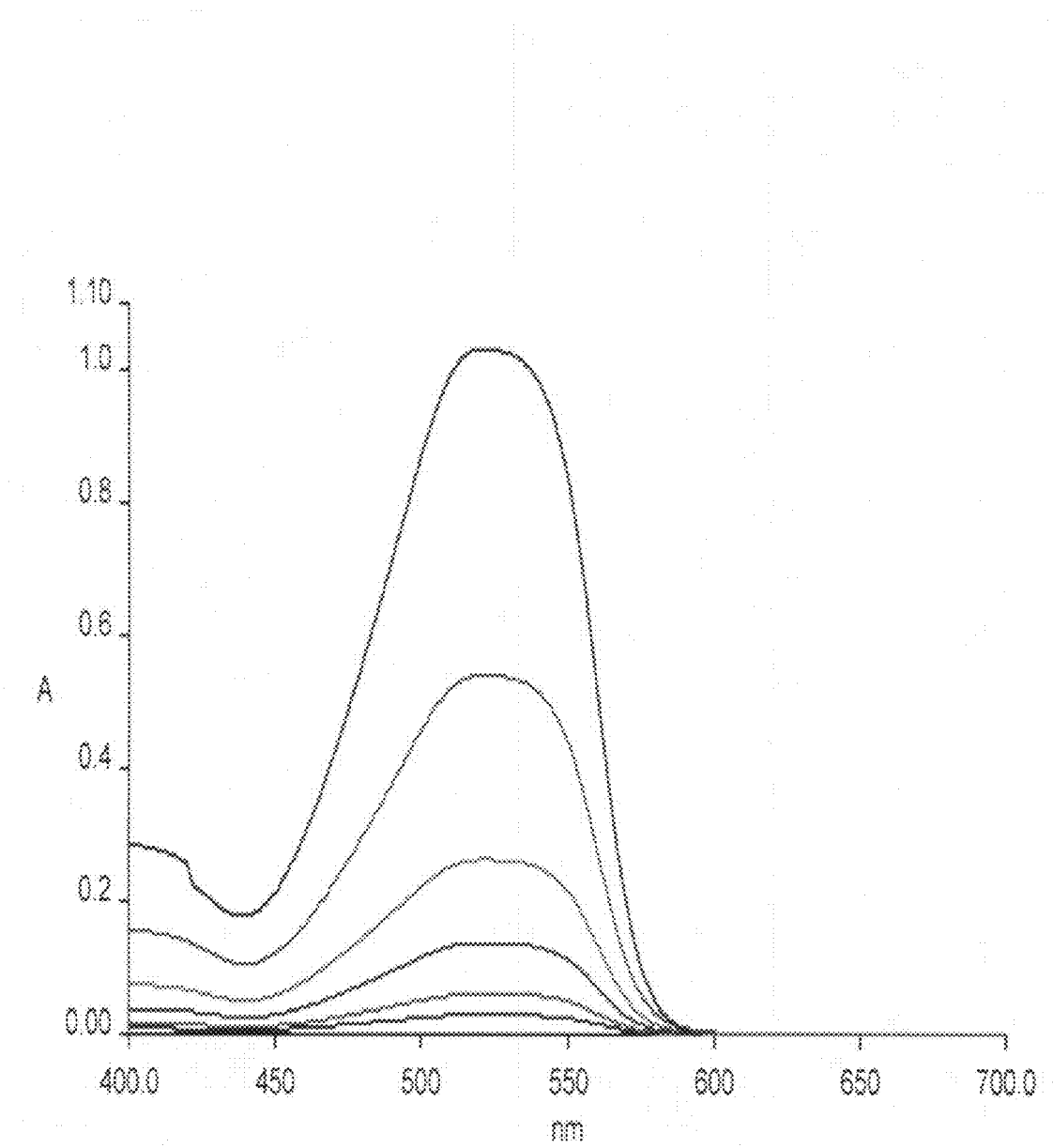
FIG. 7B shows Visible Spectra of Std Magenta Colorant from 0.54 mg/L to 17.3 mg/L.

The absorbance increases linearly with concentration from 0.5 mg/L to 17 mg/L (correlation coefficient is 0.9993) as listed in Table 1 and shown in FIGS. 7A and 7B.

Absorbance=0.06×(mg/L)

TABLE 1

Magenta Colorant Vs absorbance

| Concentration of Magenta colorant mg/L | Absorbance value at 520 nm |
|---|---|
| 0.5428 | 0.0293 |
| 1.086 | 0.0605 |
| 2.171 | 0.1368 |
| 4.343 | 0.2626 |
| 8.685 | 0.5398 |
| 17.370 | 1.0310 |

Beer's law was also found to hold for absorption by thin Magenta ink prints at O.D. of 1.1 to 1.65 and containing 0.196 g to 0.321 g of colorant per square meter of print, as determined by this invention method (see Table 2, FIG. 10).

TABLE 2

Colorant per area Vs O.D. of magenta prints

| Magenta Colorant in print g/m2 | O.D. (E) |
| --- | --- |
| 0.3209 | 1.65 |
| 0.3196 | 1.65 |
| 0.2940 | 1.50 |
| 0.2916 | 1.50 |
| 0.1979 | 1.20 |
| 0.1960 | 1.20 |
| 0.2712 | 1.45 |
| 0.2386 | 1.35 |
| 0.2032 | 1.20 |
| 0.1676 | 1.10 |
| 0.3196 | 1.60 |
| 0.3091 | 1.50 |
| 0.2627 | 1.35 |
| 0.2220 | 1.25 |

Absorptivity Coefficient of Cyan Colored Pigment

For the determination of the absorptivity coefficient of the Cyan colorant, 2.500±0.5 mg were weighed on a microbalance, accurate to 0.1 mg, and the colorant was dissolved in 250 ml of 1-methyl naphthalene. The resulting solution was diluted by a factor of 5 in order bring the absorbance near or below 1.0. The absorbance of the dilute solution was measured on the Perkin Elmer Lambda 40 UV-Visible spectrophotometer between 550-850 nm The spectrophotometer is calibrated monthly according to the manufacturers recommendations using ISO 9001 procedures and NIST standards. The spectrophtotometer is balanced just prior to analysis by scanning solvent only in both the reference cell and the sample cell.

The sample cell is filled with the Cyan solution and then placed in the sample port position and a spectrophotometric curve is scanned. The absorbance at the wavelength of maximum absorption is recorded and the absorptivity coefficient is calculated as $$a\lambda = \left(\frac{A}{c}\right)$$

Pure Cyan colorant at c=2.0 mg/Liter has A=0.8212, hence the absorptivity coefficient is $a_\lambda$=0.8212/2.0=0.4106 liter·mg$^{-1}$·cm$^{-1}$.

Figure 8A:
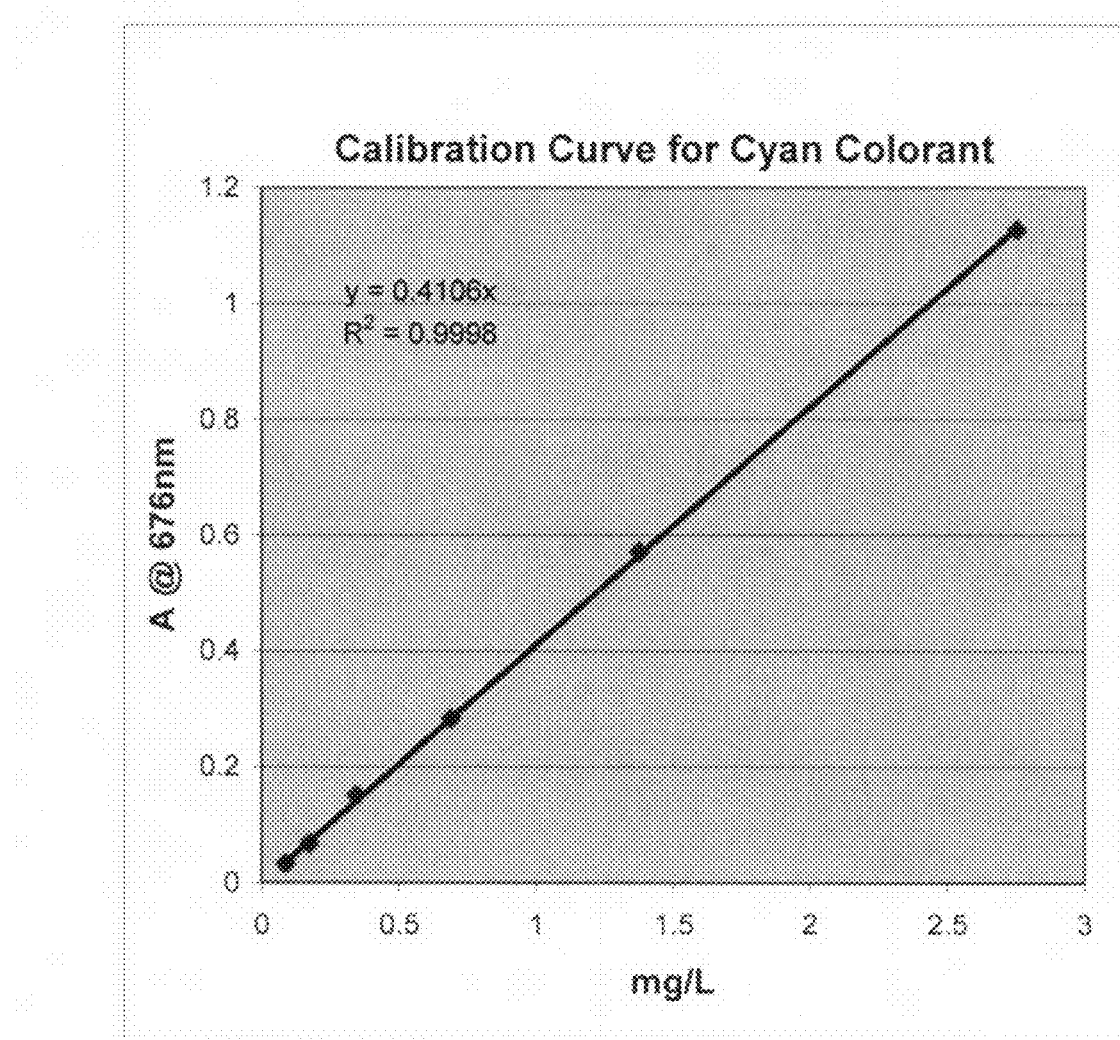
FIG. 8A shows a calibration curve (absorbance [x axis] v. mg/L [y axis]) for cyan colorant.
Figure 8B:
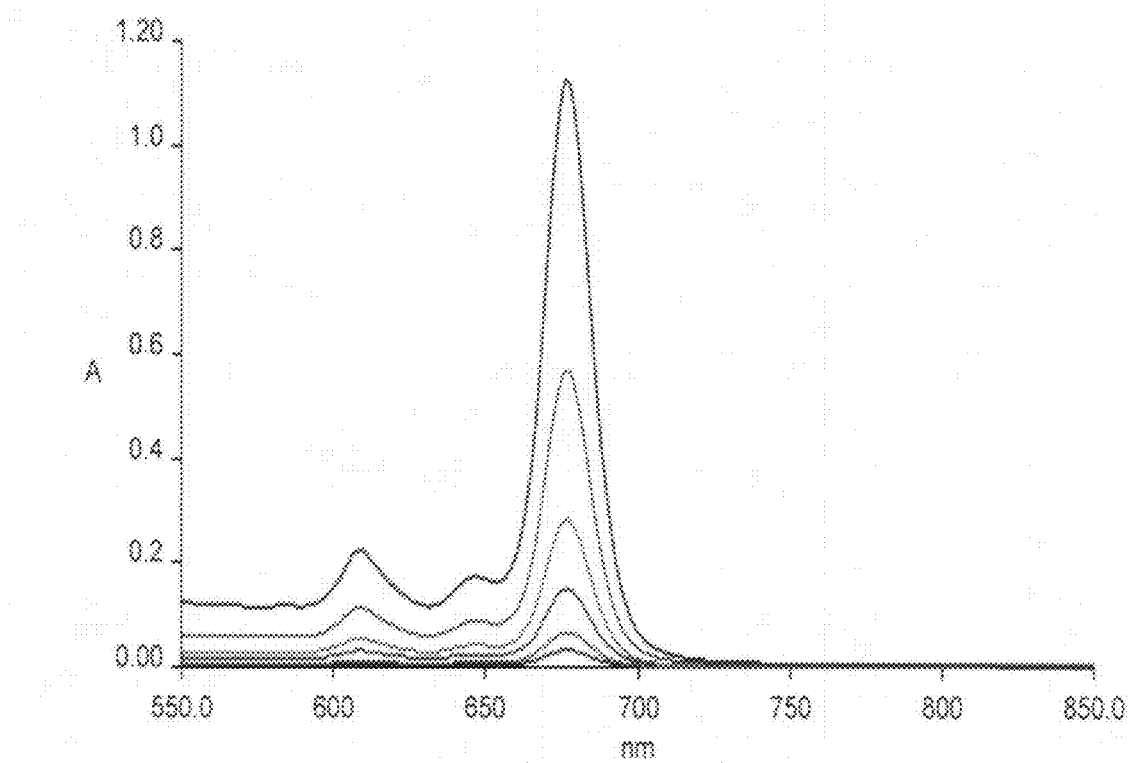
FIG. 8B shows Visible Spectra of Pigment Blue 15 0.08604-2.7534 mg/L.

The absorbance increases linearly with concentration as listed in Table 3 and shown in FIG. 8. The correlation coefficient is 0.9998.

TABLE 3

Cyan Colorant Vs absorbance

| Concentration of Cyan colorant mg/L | Absorbance value at 676 nm |
| --- | --- |
| 0.08604 | 0.0329 |
| 0.1721 | 0.0672 |
| 0.3442 | 0.1515 |
| 0.6884 | 0.2827 |
| 1.3767 | 0.5709 |
| 2.7534 | 1.1268 |

Absorptivity Coefficient of Yellow Colored Pigment

For the determination of the absorptivity coefficient of the Yellow colorant 2.5±0.5 mg were weighed on a microbalance, accurate to 0.1 mg, and the colorant was dissolved in 250 ml of o-dichlorobenzene. The absorbance of the resulting solution was measured on the Perkin Elmer Lambda 40 UV-Visible spectrophotometer between 350 nm-550 nm The spectrophotometer is calibrated monthly according to the manufacturers recommendations using ISO 9001 procedures and NIST standards. The spectrophotometer is balanced just prior to analysis by scanning solvent only in both the reference cell and the sample cell.

The sample cell is filled with the Yellow solution and then placed in the sample port position and a spectrophotometric curve is scanned. The absorbance at the wavelength of maximum absorption (430 nm) is recorded and the absorptivity coefficient is calculated as $$a_\lambda = A/c$$

Pure Yellow colorant at c=9.94 mg/Liter has A=1.1004, hence the absorptivity coefficient is $a_\lambda$=1.1004/9.94=0.1107 liter·mg$^{-1}$·cm$^{-1}$.

Figure 9A:
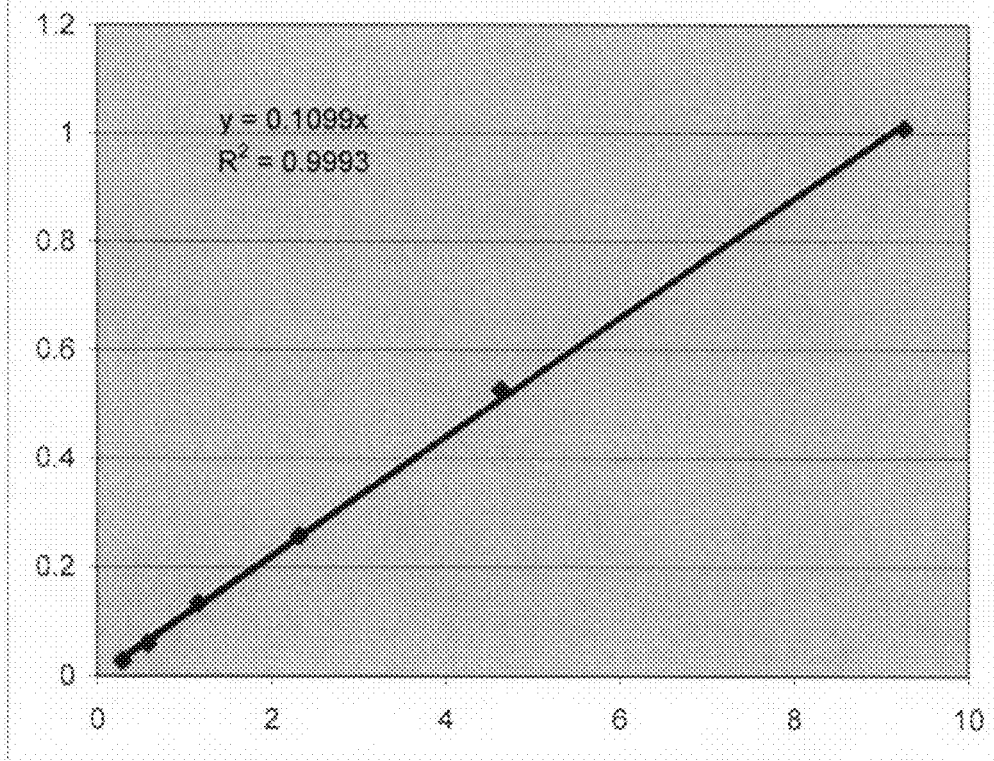
FIG. 9A shows a calibration curve (absorbance [x axix] v. mg/L [y axix]) for Std Yellow colorant.
Figure 9B:
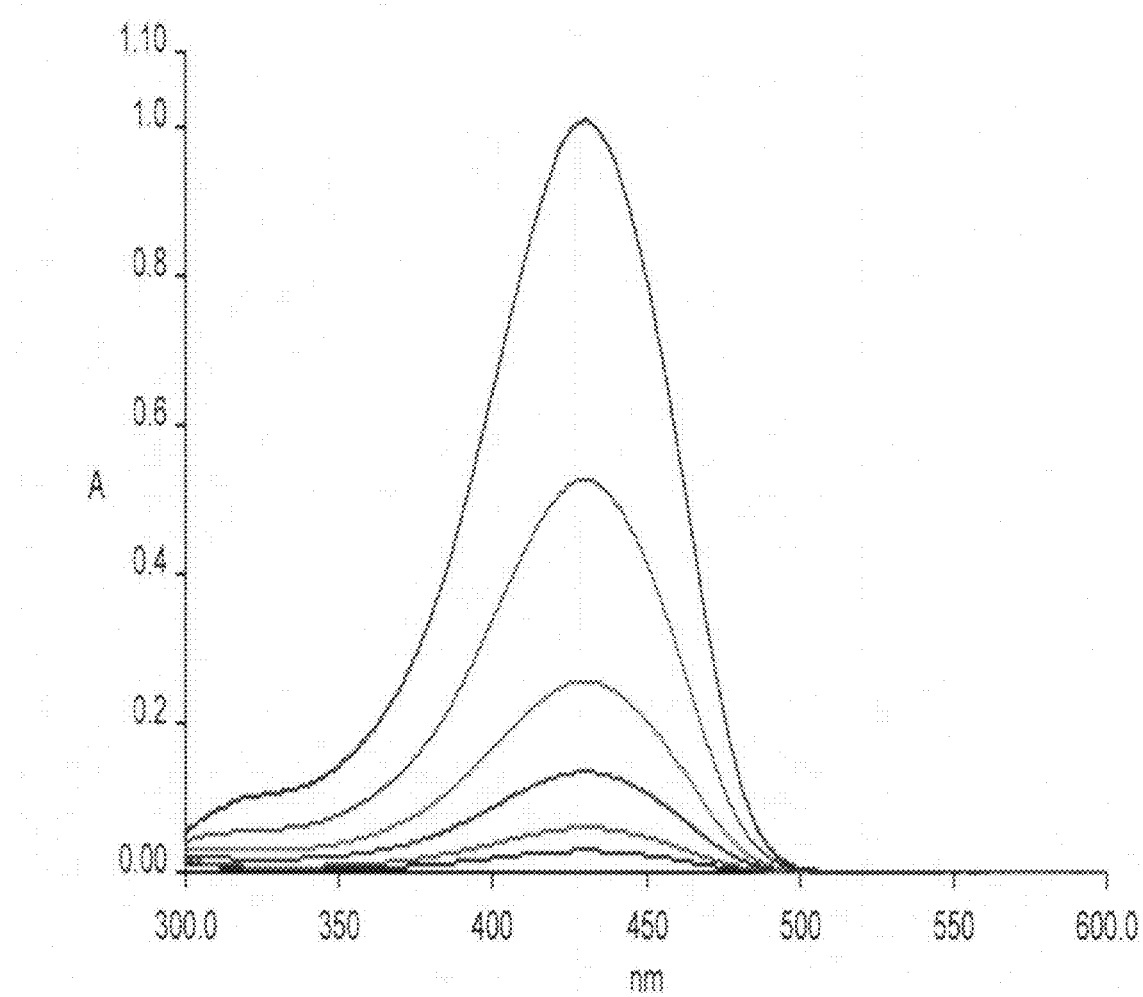
FIG. 9B shows Visible Spectra of Std Yellow colorant 0.28 mg/L to 9.26 mg/L.

The absorbance increases linearly with concentration from 0.29 mg/L to 9.2 mg/L (correlation coefficient is 0.9993) as listed in Table 4 and shown in FIG. 9A. Absorbance=0.1099× (mg/L) Visible spectra are illustrated in FIG. 9B.

TABLE 4

Yellow colorant Vs absorbance

| Concentration of Std Yellow Colorant (mg/L) | Absorbance value at 430 nm |
| --- | --- |
| 0.28925 | 0.0281 |
| 0.5785 | 0.0588 |
| 1.157 | 0.1334 |
| 2.314 | 0.2574 |
| 4.628 | 0.5261 |
| 9.256 | 1.0079 |

Figure 11:
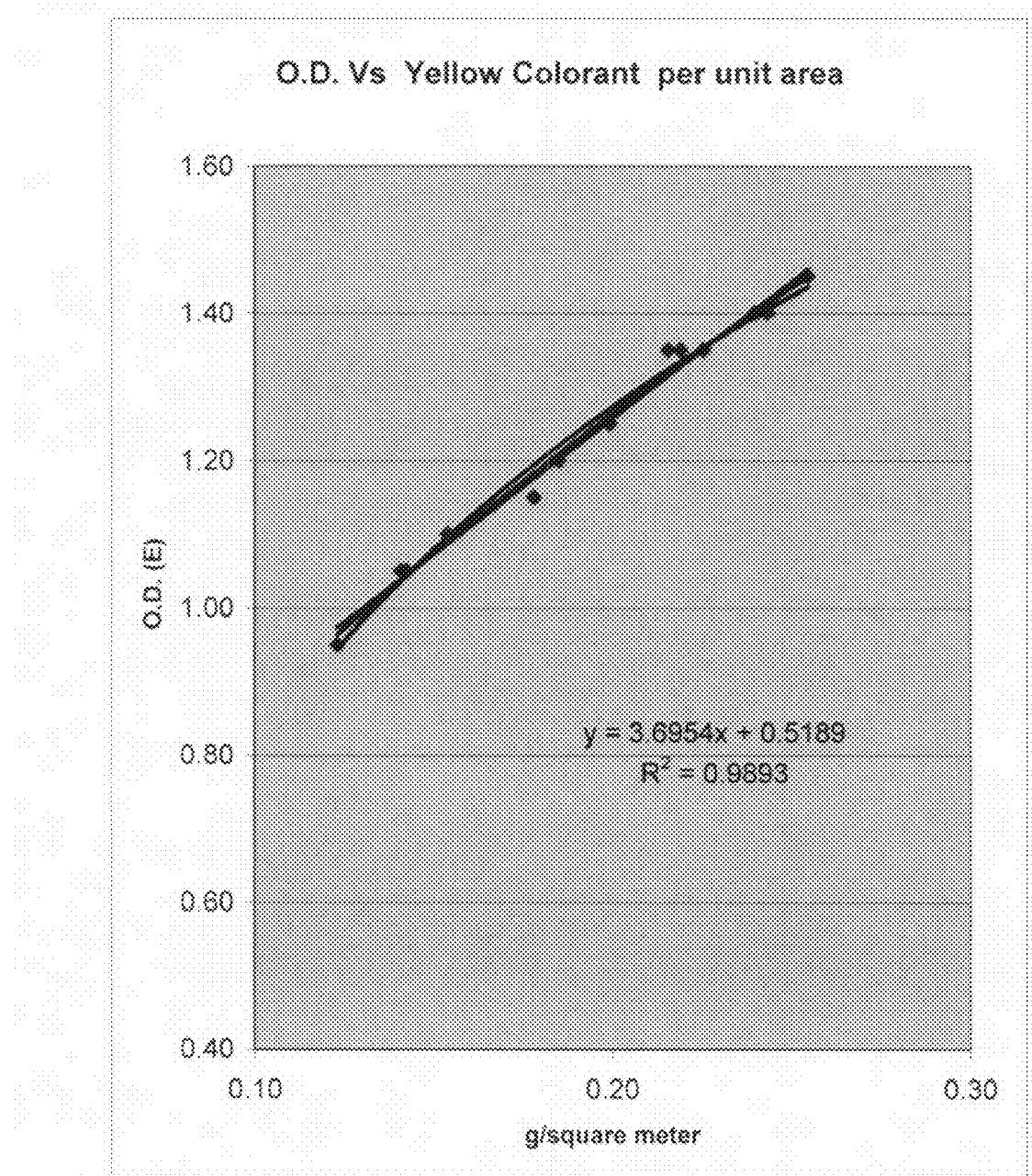
FIG. 11 shows Plot of Colorant content Vs O.D. of Yellow prints.

Beer's law also holds for absorption by thin Yellow ink prints at O.D. 0.95 to 1.35 and containing 0.123 g to 0.243 g of colorant per square meter of print as determined by this invention method (Table 5, FIG. 11).

TABLE 5

Colorant content Vs O.D. Yellow prints

| Amount of Yellow colorant in print g/m² | O.D. (E) |
| --- | --- |
| 0.24320 | 1.40 |
| 0.23980 | 1.40 |
| 0.21900 | 1.35 |
| 0.21550 | 1.35 |
| 0.14080 | 1.05 |
| 0.14200 | 1.05 |
| 0.19920 | 1.25 |
| 0.17800 | 1.15 |
| 0.14240 | 1.05 |
| 0.12300 | 0.95 |
| 0.25450 | 1.45 |
| 0.22530 | 1.35 |
| 0.18500 | 1.20 |
| 0.15380 | 1.10 |

Calculating Ink Mileage of Magenta Ink Prints

The colored taggant in the Magenta ink prints, having area 5.670×10$^{-4}$ m², was measured by dispersing in methylene chloride by sonication for 1 minute, followed by addition of 50% acidified aqueous ethanol (2% sulfuric acid in 50/50 ethanol water v/v) and sonication for 5 minutes. The resulting mixture was diluted to 50 ml with acidified ethanol in a volumetric flask. The solution was filtered through a 1.0 micron glass fiber membrane and scanned on the spectrophotometer between 400 nm-700 nm. The absorbance at the wavelength of maximum absorption (518 nm) was recorded. The baseline absorption at 650 nm was also measured and subtracted from the absorbance at 518 nm. This corrects for scattering of light from small, non-colored, colloidal particles that may be present. The amount of the magenta colorant was calculated from the corrected absorbance ($A_c$) value and the absorptivity coefficient using Beer's law.

The amount of pigment (mg) per print area=$(A_c \times V)/a_\lambda$, where $A_c$=corrected sample absorbance·cm$^{-1}$, V=sample volume in liters, $a_\lambda$=absorptivity coefficient=0.0600 liter·mg$^{-1}$·cm$^{-1}$.

If $A_c$=-0.107, V=0.050 L, and signature print area=5.670×10$^{-4}$ m$^2$ then, amount of pigment/5.670×10$^{-4}$ m$^2$=(0.107×0.50)/0.06=0.0892 mg or 8.92×10$^{-8}$ Kg. Hence the color efficiency=5.670×10$^{-4}$ m$^2$/(8.92×10$^{-8}$ Kg)=6359 m$^2$/Kg colorant.

The ink mileage at a given O.D. can be calculated if the amount of Magenta chromophore in the ink is known.

ink mileage=(color efficiency m$^2$/Kg×O.D.)×% colorant in ink/100

If % colorant in the ink=11.7 and the O.D.=1.093 then:

Ink mileage=(6359 m$^2$/Kg×1.093×11.7)/100=813.2 m$^2$/Kg of ink

The precision of the ink mileage determination of Magenta heatset inks by the present invention method was determined based on 18 replicate determinations of prints made from the same batch of ink at O.D. of 1.085-1.100.

Figure 12:
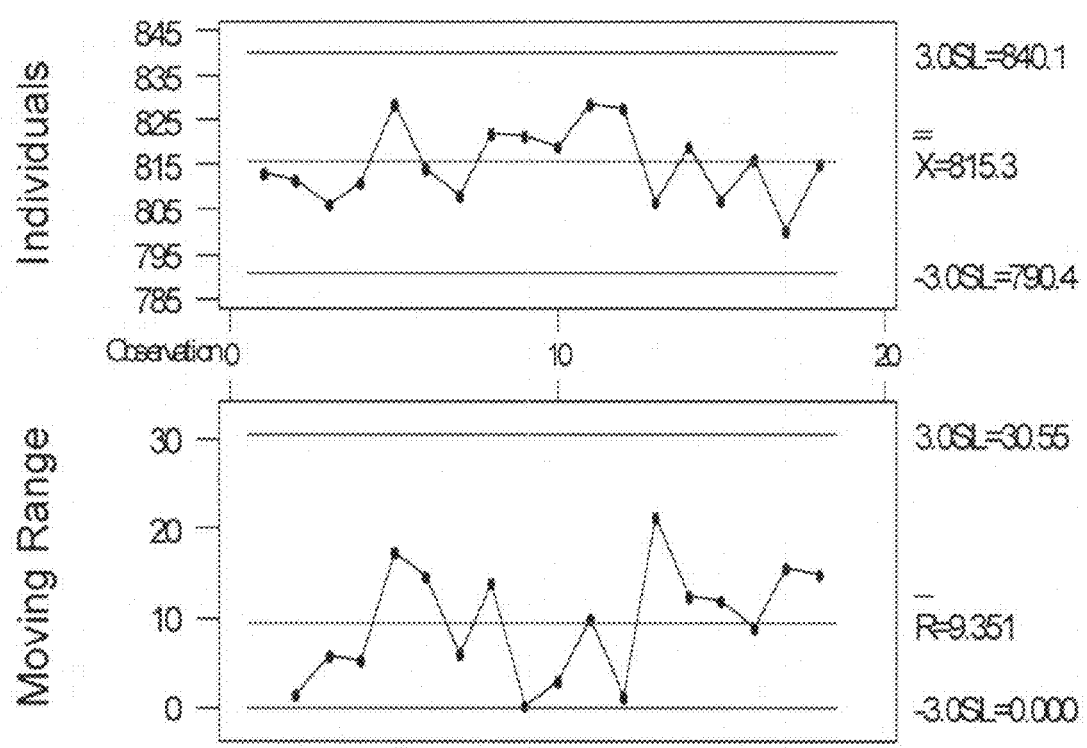
FIG. 12 shows I and MR Chart for precision Signature Mileage of Magenta prints.

The average signature mileage was 815.3 m$^2$/Kg with a Standard Deviation of 8.3 and Relative Standard Deviation of 1.0%. The range was 800.2 to 828.7 m$^2$/Kg. The results are summarized in Table 6 below. The I and MR chart is shown in FIG. 12.

TABLE 6

Precision of Ink mileage for magenta inks

| O.D. | Magenta Mileage | Average Mileage |
|---|---|---|
| Ave. of 4 | m$^2$ × O.D./kg Ink | 815.3 m2/Kg |
|  |  | 369.8 lbs/Kg |
| 1.093 | 813.2 | STD Dev. 8.30E+00 |
| 1.095 | 811.7 | RSD = 1.0% |
| 1.095 | 806.1 |  |
| 1.085 | 811.2 |  |
| 1.095 | 828.6 |  |
| 1.088 | 814.0 |  |
| 1.088 | 808.0 |  |
| 1.099 | 821.8 |  |
| 1.094 | 821.7 |  |
| 1.088 | 818.8 |  |
| 1.095 | 828.7 |  |
| 1.090 | 827.6 |  |
| 1.090 | 806.3 |  |
| 1.097 | 818.8 |  |
| 1.086 | 807.0 |  |
| 1.107 | 815.9 |  |
| 1.089 | 800.2 |  |
| 1.100 | 815.1 |  |

Calculating Ink Mileage of Cyan Ink Prints

The colorant of the Cyan ink prints, having area 5.670×10$^{-4}$ m$^2$, was dissolved in 1-methylnaphthalene. The final volume was adjusted to 50 ml a volumetric flask. The solution was scanned on the spectrophotometer between 550 nm-850 nm and the absorbance at the wavelength of maximum absorption (676 nm) was recorded. The baseline absorption at 850 nm was also measured and subtracted from the absorbance at 676 nm. This corrects for scattering of light from small non-colored colloidal particles that may be present. The amount of the magenta colorant was calculated from the corrected absorbance ($A_c$) value and the absorptivity coefficient using Beer's law.

Amount of pigment (mg) per print area=$(Ac \times V)/a\lambda$ where Ac=corrected sample absorbance·cm−1

V=sample volume in liters =a$\lambda$=absorptivity coefficient=0.3781 liter·mg−1·cm−1.

If $A_c$=0.6033, V=0.050 L, and signature print area=5.670×10$^{-4}$ m$^2$ then, amount of pigment/5.670×10$^{-4}$ m$^2$=(0.6033×0.50)/0.3781=0.0798 mg or 7.98×10$^{-8}$ Kg Hence the color efficiency=5.670×10$^{-4}$ m$^2$/(7.98×10$^{-8}$ Kg)=7105 m$^2$/Kg.

The ink mileage at a given O.D. can be calculated if the amount of Magenta chromophore in the ink is known.

Ink mileage=(color efficiency m$^2$/Kg×O.D.×% colorant in ink)/100

If % colorant in the ink=13.1 and the O.D.=1.010 then

Ink mileage=(7105 m$^2$/Kg×0.979×13.1)/100=911.2 m$^2$/Kg of ink

Figure 13:
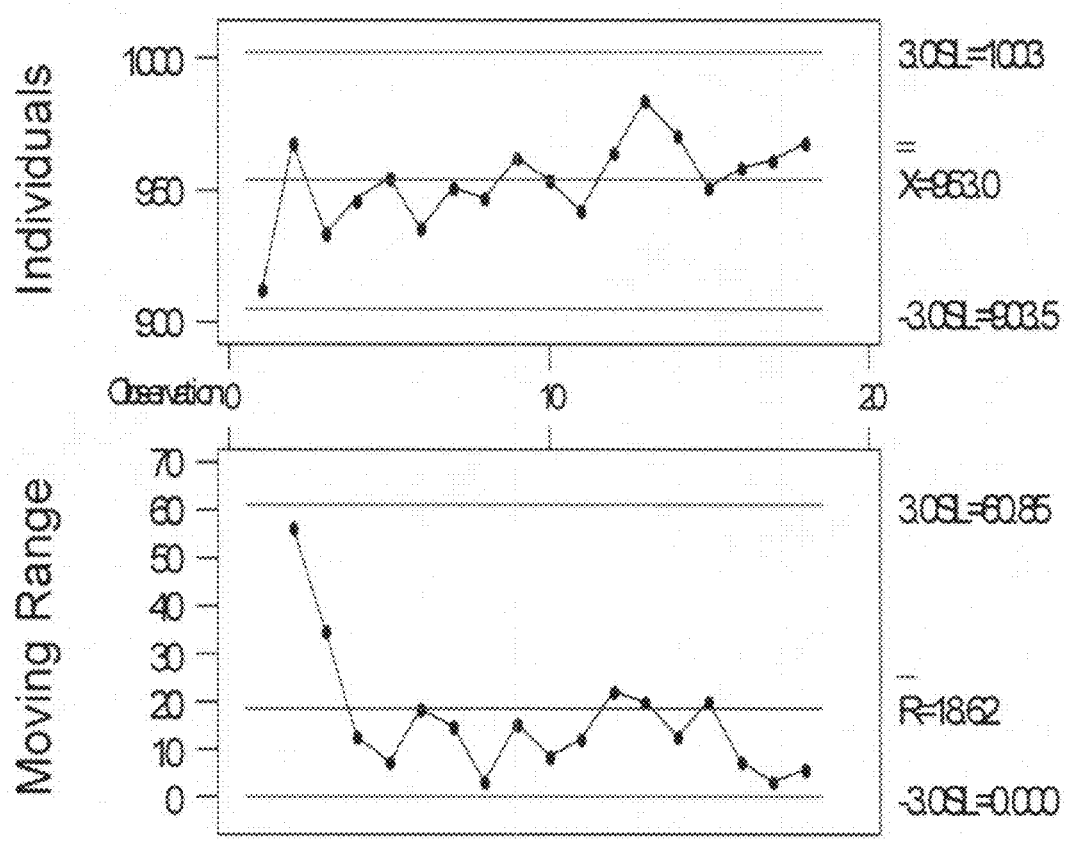
FIG. 13 shows I and MR Chart for precision Signature Mileage of Cyan prints.

The precision of the ink mileage for the Cyan heatset inks was determined based on 18 replicate determinations of prints from the same batch of ink at O.D. 0.977-1.029. The average signature mileage was 953 m$^2$/Kg with a Standard Deviation of 16.5 and Relative Standard Deviation of 1.7. The range was 911.5 to 983.6 m$^2$/Kg. The results are summarized in Table 7 below. The I and MR cart is shown in FIG. 13.

TABLE 7

Precision of Ink mileage for cyan inks

| O.D. | Cyan Ink Mileage | Average Ink Mileage |
|---|---|---|
| Ave. of 4 | m$^2$ × O.D./kg Ink | 953.0 m2/Kg |
|  |  | 432.3 m$^2$/lb |
| 0.979 | 911.5 | STD Dev = 16.5 |
| 1.010 | 967.8 | RSD 1.73% |
| 1.020 | 933.2 |  |
| 0.991 | 945.8 |  |
| 0.972 | 953.6 |  |
| 1.007 | 935.0 |  |
| 0.997 | 950.0 |  |
| 0.982 | 946.5 |  |
| 1.023 | 961.9 |  |
| 0.972 | 953.5 |  |
| 1.009 | 941.4 |  |
| 0.977 | 963.6 |  |
| 1.017 | 983.6 |  |
| 0.982 | 970.6 |  |
| 1.008 | 950.2 |  |
| 0.992 | 957.8 |  |
| 1.029 | 961.1 |  |
| 1.004 | 967.2 |  |

Calculating Ink Mileage of Yellow Ink Prints

The colorant in the Yellow ink prints, having area 5.670×10$^{-4}$ m$^2$, was dissolved in o-dichlorobenzene in a 50 ml beaker. The final volume was adjusted to 50 ml a volumetric flask. The solution was scanned on the spectrophotometer between 350 nm-550 nm. The absorbance at the wavelength of maximum absorption (430 nm) was recorded. The baseline absorption at 550 nm was also measured and subtracted from the absorbance at 430 nm. This corrects for scattering of light from small non-colored colloidal particles that may be present. The amount of the magenta colorant was calculated from the corrected absorbance ($A_c$) value and the absorptivity coefficient using Beer's law.

Amount of pigment (mg) per print area=$(A_c \times V)/a_\lambda$ where $A_c$=corrected sample absorbance·cm$^{-1}$ V=sample volume in liters $a_\lambda$=absorptivity coefficient=0.1107 liter·mg$^{-1}$·cm$^{-1}$.

If $A_c$=0.1587, V=0.050 L, and signature print area=5.670×10$^{-4}$ m$^2$ then, amount of pigment/5.670×10$^{-4}$ m$^2$=(0.1587×0.50)/0.1107=0.0717 mg or 7.17×10$^{-8}$ Kg. Hence the color efficiency=5.670×10$^{-4}$ m$^2$/(7.17×10$^{-8}$ Kg)=7908 m$^2$/Kg.

The ink mileage at a given O.D. can be calculated if the amount of Magenta chromophore in the ink is known.

Ink mileage=(color efficiency m$^2$/Kg×O.D.×% colorant in ink)/100

If % colorant in the ink=10.5 and the O.D.=0.923 then,

Ink mileage=(7908 m$^2$/Kg×0.923×10.5)/100=766.4 m$^2$/Kg of ink

The precision of the ink present mileage by the present invention method for the Yellow heatset inks was determined based on 18 replicate determinations of prints from the same batch of ink. At O.D. 0.922-0.939.

Figure 14:
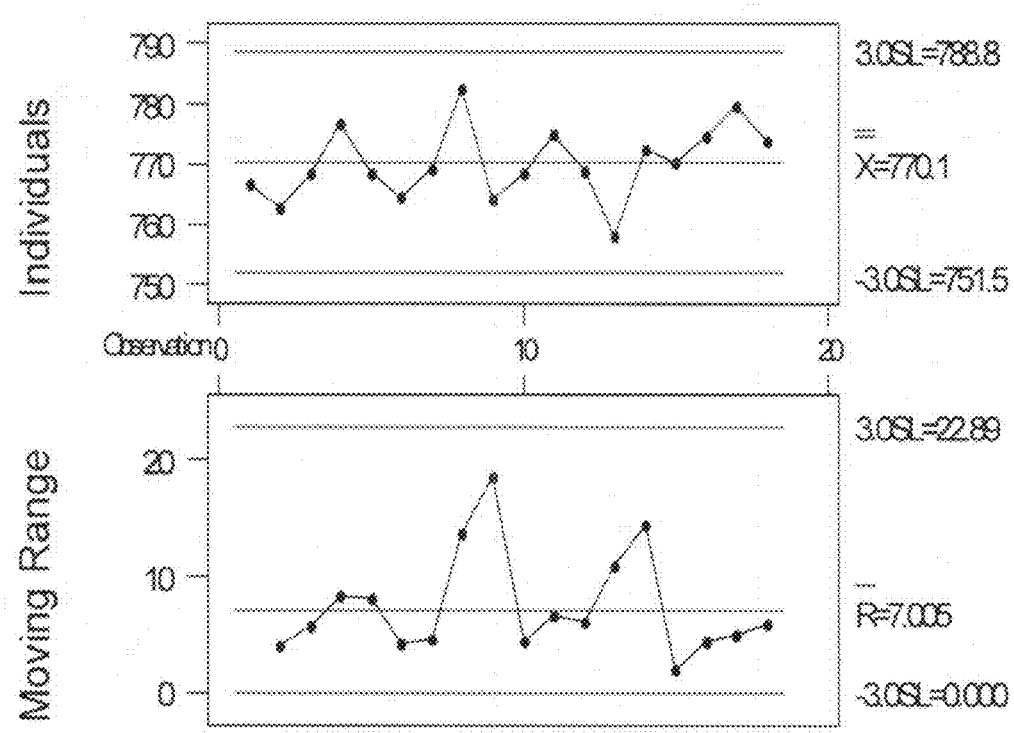
FIG. 14 shows I and MR Chart for precision Signature Mileage of Yellow prints.

The average ink mileage was 770.1 m$^2$/Kg with a Standard Deviation of 6.2 and Relative Standard Deviation of 0.8%. The range was 757.7 to 782.6 m2/Kg. The results are summarized in Table 8 below. The I and MR chart is shown in FIG. 14.

TABLE 8

Precision of Ink mileage for yellow inks

| O.D. | Ink Mileage Yellow colorant | Average ink Mileage |
|---|---|---|
| Ave. of 4 | m$^2$ × O.D./kg Ink | 770.1 m$^2$/Kg |
|  |  | 349.3 m$^2$/lb |
| 0.923 | 766.7 | STD Dev. = 6.21 |
| 0.931 | 762.7 | RSD = 0.81% |
| 0.928 | 768.4 |  |
| 0.928 | 776.7 |  |
| 0.924 | 768.5 |  |
| 0.934 | 764.2 |  |
| 0.938 | 768.9 |  |
| 0.928 | 782.6 |  |
| 0.922 | 763.9 |  |

TABLE 8-continued

Precision of Ink mileage for yellow inks

| O.D. | Ink Mileage Yellow colorant | Average ink Mileage |
|---|---|---|
| 0.932 | 768.3 |  |
| 0.937 | 774.9 |  |
| 0.936 | 768.7 |  |
| 0.922 | 757.7 |  |
| 0.931 | 772.3 |  |
| 0.922 | 770.2 |  |
| 0.939 | 774.6 |  |
| 0.935 | 779.6 |  |
| 0.932 | 773.6 |  |

A summary of the results and precision data for the determination of the Ink mileage of Yellow, Magenta and Cyan inks by the present invention is listed in Table 9 below.

TABLE 9

Precision of Ink mileage measurement for Yellow, Magenta and Cyan inks

| Sample | Mean Ink Mileage (m$^2$/Kg) | STD Dev. (1 Sigma) | RSD | Mean +/− 3 Sigma |
|---|---|---|---|---|
| Yellow | 770 | 6.2 | 0.8% | 770 +/− 18.6 or +/− 2.4% |
| Magenta | 815 | 8.3 | 1.0% | 815 +/− 24.9 or +/− 3.1% |
| Cyan | 953 | 16.5 | 1.7% | 953 +/− 49.5 or +/− 5.2% |

EXAMPLE 1

Printing Magenta Ink and Predicting Its Ink Mileage

The capability of the present invention method to accurately differentiate and predict ink mileage for heatset magenta inks was illustrated by determining the ink mileage of standard magenta ink before and after dilution with solvent.

A standard magenta ink at 10.66% colorant was diluted by a factor of 10.6% resulting in ink with 9.53% colorant content. The inks were printed on uncoated paper at O.D. of 1.1+/−0.03. The ink mileage was then measured as described previously in the Section entitled "Calculating Ink Mileage of Magenta Ink Prints". The Ink mileage of the diluted ink was found to be 230.1 m$^2$/kg which is 10.3% lower relative to the ink mileage of standard ink, of 256.6 m$^2$/Kg ink. The deviation of the ink mileage reduction from that predicted by the dilution factor is less than 3% relative, illustrating good accuracy. The relative standard deviation of the ink mileage results was 1.04% for the diluted ink and 2.06% for the standard ink. See Table 10 below.

TABLE 10

Comparison of colorant content and ink mileage before and after dilution of Magenta in on uncoated paper

| O.D. (T) | O.D. (T) corrected. | Ink Mileage m$^2$ × OD × C.F./kg Ink | Average Mileage m$^2$/Kg ink | % relative change in ink mileage -vs- std |
|---|---|---|---|---|
| Magenta ink diluted 9.53% colorant −10.6% colorant -Vs Std |  |  |  |  |
| 1.127 | 0.987 | 229.5 | 230.1 | −10.3 |
| 1.126 | 0.985 | 232.6 | 104.4 |  |

TABLE 10-continued

Comparison of colorant content and ink mileage before and after dilution of Magenta in on uncoated paper

| O.D. (T) | O.D. (T) corrected. | Ink Mileage $m^2 \times OD \times C.F./kg$ Ink | Average Mileage $m^2/Kg$ ink | % relative change in ink mileage -vs- std |
|---|---|---|---|---|
| 1.132 | 0.995 | 227.0 | | |
| 1.131 | 0.994 | 231.3 | STD Dev = 2.4 | |
| | | | RSD = 1.04% | |
| Std Ink 10.66% colorant | | | | |
| 1.142 | 1.012 | 252.8 | 256.6 | |
| 1.150 | 1.025 | 259.5 | 116.4 | |
| 1.133 | 0.997 | 262.5 | | |
| 1.145 | 1.016 | 251.5 | | |
| | | | STD Dev = 5.3 | |
| | | | RSD 2.06% | |

EXAMPLE 2

Printing Yellow Ink and Predicting Its Ink Mileage

The capability of the present invention method to accurately differentiate and predict ink mileage for heatset yellow inks was illustrated by determining the ink mileage of standard yellow ink before and after dilution with solvent.

A standard yellow ink at 6.5% colorant was diluted by a factor of 14.7% resulting in ink with 5.58% colorant content. The inks were printed on uncoated paper at O.D 0.94+/−0.03. and on coated Leneta paper at O.D of 1.05+/−0.03.

The ink mileage was then measured as described previously in the Section entitled "Calculating Ink Mileage of Yellow Ink Prints". The Ink mileage of the diluted ink on uncoated paper was found to be 507.6 $m^2$/kg which is 14.0% lower relative to the ink mileage of standard ink on uncoated paper of 590.0 $m^2$/Kg ink. The deviation of the ink mileage reduction found from that predicted by the dilution factor is less than 5% relative. The relative standard deviation of the ink mileage results was 2.99% for the diluted ink and 1.75% for the standard ink. See Table 11 below.

TABLE 11

Comparison of colorant content and ink mileage before and after dilution of Yellow ink on uncoated paper

| O.D. (T) | O.D. (T) corrected | Ink Mileage $m^2 \times$ OD $\times$ C.F./Kg Ink | Average Mileage $m^2/Kg$ ink | % relative change in ink mileage -vs- std |
|---|---|---|---|---|
| Yellow ink diluted 5.58% colorant −14.7% colorant -vs std ink | | | | |
| 0.951 | 1.005 | 517.5 | 507.6 | −14.0 |
| 0.963 | 1.034 | 516.2 | 230.3 | |
| 0.915 | 0.921 | 491.9 | | |
| 0.933 | 0.962 | 486.3 | | |
| 0.948 | 0.997 | 509.7 | STD Dev = 15.2 | |
| 0.936 | 0.969 | 524.1 | | |
| | 0.981 | | RSD 2.99% | |
| Std Yellow ink 6.54% colorant | | | | |
| 0.953 | 1.009 | 587.0 | 590.0 | |
| 0.960 | 1.027 | 597.4 | 267.6 | |

TABLE 11-continued

Comparison of colorant content and ink mileage before and after dilution of Yellow ink on uncoated paper

| O.D. (T) | O.D. (T) corrected | Ink Mileage $m^2 \times$ OD $\times$ C.F./Kg Ink | Average Mileage $m^2/Kg$ ink | % relative change in ink mileage -vs- std |
|---|---|---|---|---|
| 0.976 | 1.067 | 597.0 | | |
| 0.979 | 1.074 | 602.1 | | |
| 0.974 | 1.062 | 577.5 | STD Dev = 10.3 | |
| 0.950 | 1.002 | 579.0 | RSD 1.75% | |

The Ink mileage of the diluted yellow ink on coated paper was found to be 719.4 $m^2$/kg which is 14.7% lower relative to the ink mileage of standard ink on uncoated paper of 843.6 $m^2$/Kg ink. This is exactly what was predicted by the dilution factor as determined by the colorant content, and clearly illustrates that accuracy of the method is very good. The relative standard deviation of the ink mileage results was 2.99% for the diluted ink and 1.75% for the standard ink. See Table 12 below.

TABLE 12

Comparison of colorant content and ink mileage before and after dilution of Yellow ink on coated paper

| O.D. (T) | O.D. (T) corrected | Ink Mileage $m^2 \times$ OD $\times$ C.F./kg Ink | Average Mileage $m^2/Kg$ ink | % relative change in ink mileage -vs- std |
|---|---|---|---|---|
| Yellow ink diluted 5.58% colorant −14.7% colorant -vs std ink | | | | |
| 1.064 | 1.060 | 713.4 | 719.4 $m^2$/Kg | −14.7 |
| 1.069 | 1.073 | 729.8 | 326.3 $m^2$/lb | |
| 1.059 | 1.048 | 718.2 | | |
| 1.073 | 1.083 | 729.4 | | |
| 1.061 | 1.053 | 705.9 | STD Dev = 1.04 | |
| | | | RSD = 1.44% | |

TABLE 12-continued

Comparison of colorant content and ink mileage before and after dilution of Yellow ink on coated paper

| O.D. (T) | O.D. (T) corrected | Ink Mileage m² × OD × C.F./kg Ink | Average Mileage m²/Kg ink | % relative change in ink mileage -vs- std |
|---|---|---|---|---|
| Std Yellow ink 6.54% colorant | | | | |
| 1.009 | 0.929 | 842.2 | 843.6 m²/Kg | |
| 1.065 | 1.063 | 859.2 | 382.6 m²/lb | |
| 1.067 | 1.068 | 807.8 | | |
| 1.060 | 1.050 | 841.1 | | |
| 1.003 | 0.916 | 846.8 | STD Dev = 19.9 | |
| 0.952 | 0.909 | 864.3 | RSD = 2.36% | |

EXAMPLE 3

Printing Cyan Ink and Predicting Its Ink Mileage

The capability of the present invention method to accurately differentiate and predict ink mileage for heatset cyan inks was illustrated by determining the ink mileage of standard Cyan ink before and after dilution with solvent.

A standard Cyan ink at 10.55% colorant was diluted by a factor of 18.7% resulting in ink with 8.58% colorant content. The inks were printed on uncoated paper at O.D of 1.1+/−0.03. The ink mileage was then measured as described previously in the Section entitled "Calculating Ink Mileage of Cyan Ink Prints". The Ink mileage of the diluted ink was found by this invention method to be 245.1 m²/kg which is 19.1% lower relative to the ink mileage of standard ink, of 303.0 m²/Kg ink. The deviation of the ink mileage reduction found from that predicted by the dilution factor is 2.1% relative, which illustrates very good accuracy for the method. The relative standard deviation of the ink mileage results was 10.53% for the diluted ink and 2.76% from the standard ink. See Table 13.

TABLE 13

Comparison of colorant content and ink mileage before and after dilution of Cyan ink on uncoated paper.

| O.D. (T) | O.D. (T) corrected | Ink Mileage m² × OD × C.F./kg Ink | Average Mileage m²/Kg ink | % relative change in ink mileage -vs- std |
|---|---|---|---|---|
| Cyan ink diluted 8.58% colorant −18.7% colorant -vs- Std | | | | |
| 1.100 | 1.104 | 246.9 | 245.1 | −19.1 |
| 1.100 | 1.104 | 245.2 | 111.2 | |
| 1.100 | 1.104 | 243.8 | | |
| 1.086 | 1.077 | 244.6 | | |
| | | | STD Dev = 1.3 | |
| | | | RSD = 0.53% | |
| Std Cyan ink 10.55% colorant | | | | |
| 1.076 | 1.058 | 307.8 | 303.0 | |
| 1.086 | 1.077 | 298.5 | 137.4 | |

TABLE 13-continued

Comparison of colorant content and ink mileage before and after dilution of Cyan ink on uncoated paper.

| O.D. (T) | O.D. (T) corrected | Ink Mileage m² × OD × C.F./kg Ink | Average Mileage m²/Kg ink | % relative change in ink mileage -vs- std |
|---|---|---|---|---|
| 1.074 | 1.054 | 311.6 | | |
| 1.070 | 1.046 | 294.1 | | |
| | | | STD Dev = 8.1 | |
| | | | RSD = 2.67% | |

EXAMPLE 4

Predicting Ink Mileage of Commercially Available Cyan, Magenta and Yellow Inks Printed on Color Bar Strips The capability of this invention method to predict press mileage using small prints was demonstrated by analyzing 2 mm×2 mm areas of color bar strips of Cyan, Magenta and Yellow inks made from three ink manufacturers. The strips were removed from the printed pages by cutting and measuring using a microscope knife and a digital caliper accurate to 0.01 mm. The ink firm was dissolved in 5 mL of solvent according to the procedures described previously for each type of ink.

The ink mileage and normalized ink mileage results are listed in Tables 14 and 15 below. There is a good correlation between all the inks from manufactures 1 and 2 and between all the magenta inks from all three manufacturers.

TABLE 14

Ink mileage of Cyan Magenta and Yellow inks from color bar analysis

| Sample | % Pigment in ink | Pigment Efficiency (m²/g) | Signature Ink Mileage (m²/Kg) | Signature Ink Mileage (m²/lb) |
|---|---|---|---|---|
| Cyan 1 | 13.1% | 7.2886 | 953 | 432 |
| Cyan 2 | 12.6% | 7.6838 | 962 | 436 |
| Cyan 3 | 13.4% | 6.2574 | 849 | 385 |
| Magenta 1 | 11.7% | 6.3751 | 815 | 370 |
| Magenta 2 | 15.4% | 5.8948 | 1034 | 469 |
| Magenta 3 | 13.7% | 5.9676 | 916 | 416 |
| Yellow 1 | 10.5% | 7.8860 | 770 | 349 |
| Yellow 2 | 11.3% | 8.4331 | 904 | 410 |
| Yellow 3 | 9.1% Y174 | 8.1554 | 717 | 325 |

TABLE 15

Normalized Ink mileage from Table 14 and comparison to press mileage

| Sample | normalized Pigment in ink | normalized Pigment Efficiency (m²/g pigment) | normalized Signature ink Mileage (m²/lb ink) | Normalized Press Mileage (m²/lb) |
|---|---|---|---|---|
| Cyan 1 | 100 | 100 | 100 | 100 |
| Cyan 2 | 96 | 105 | 101 | 102 |
| Cyan 3 | 102 | 86 | 89 | 111 |
| Magenta 1 | 100 | 100 | 100 | 100 |
| Magenta 2 | 132 | 92 | 127 | 114 |
| Magenta 3 | 117 | 94 | 112 | 118 |

TABLE 15-continued

Normalized Ink mileage from Table 14 and comparison to press mileage

| Sample | normalized Pigment in ink | normalized Pigment Efficiency ($m^2$/g pigment) | normalized Signature ink Mileage ($m^2$/lb ink) | Normalized Press Mileage ($m^2$/lb) |
|---|---|---|---|---|
| Yellow 1 | 100 | 100 | 100 | 100 |
| Yellow 2 | 108 | 107 | 117 | 117 |
| Yellow 3 | 87 | 103 | 93 | 107 |

There is a discrepancy between the ink mileage measured by the present invention method and press mileage for the Yellow ink from manufacturer 3. This is probably due to the use of mixture of yellow colorants which changes slightly the absorptivity coefficient of the mixed colorant relative to the single standard yellow colorant.

The cause of discrepancy between the ink mileage measured by the present invention method and press mileage for the Cyan ink from manufacturer 3 is unknown.

EXAMPLE 5

Predicting Potential Problems in Ink Mileage of Diluted Commercial Magenta Ink

Commercial Magenta ink containing 10.9% colorant was diluted by approximately 6.4% with solvent and milled, resulting in colorant content of 10.2%. The ink mileage of the diluted ink was 609.6 $m^2$/Kg of ink at SWOP O.D. of 1.46 with a standard deviation of 2.6% as measured by the method described previously in the Section entitled "Calculating Ink Mileage of Magenta Ink Prints". This is 24% lower than the ink mileage of the original ink, 801.4 $m^2$/Kg ink at SWOP O.D. of 1.46 with standard deviation of 2.5%. The much larger than expected drop in mileage was attributed to significant bronzing as determined by reflectance spectroscopy. The diluted ink also has significantly smaller particles size and was stronger in white bleach test. The results (see Table 16 below) show that ink mileage can be significantly different than what would be expected based on colorant content and particle size, and illustrates the applicability of this invention method to predict potential problems on the press and thus avoid expensive press trial.

TABLE 16

Print mileage of magenta ink exhibiting bronzing.

| Sample | % Pigment | Mean Particle Diameter | Ink Mileage |
|---|---|---|---|
| Original ink | 10.9 | 76 nm | 801.4 $m^2$/Kg or 363.5 $m^2$/lb |
| Diluted Ink | 10.2 | 57 nm | 609.6 $m^2$/Kg or 276.5 $m^2$/lb |

EXAMPLE 6

Figure 15:
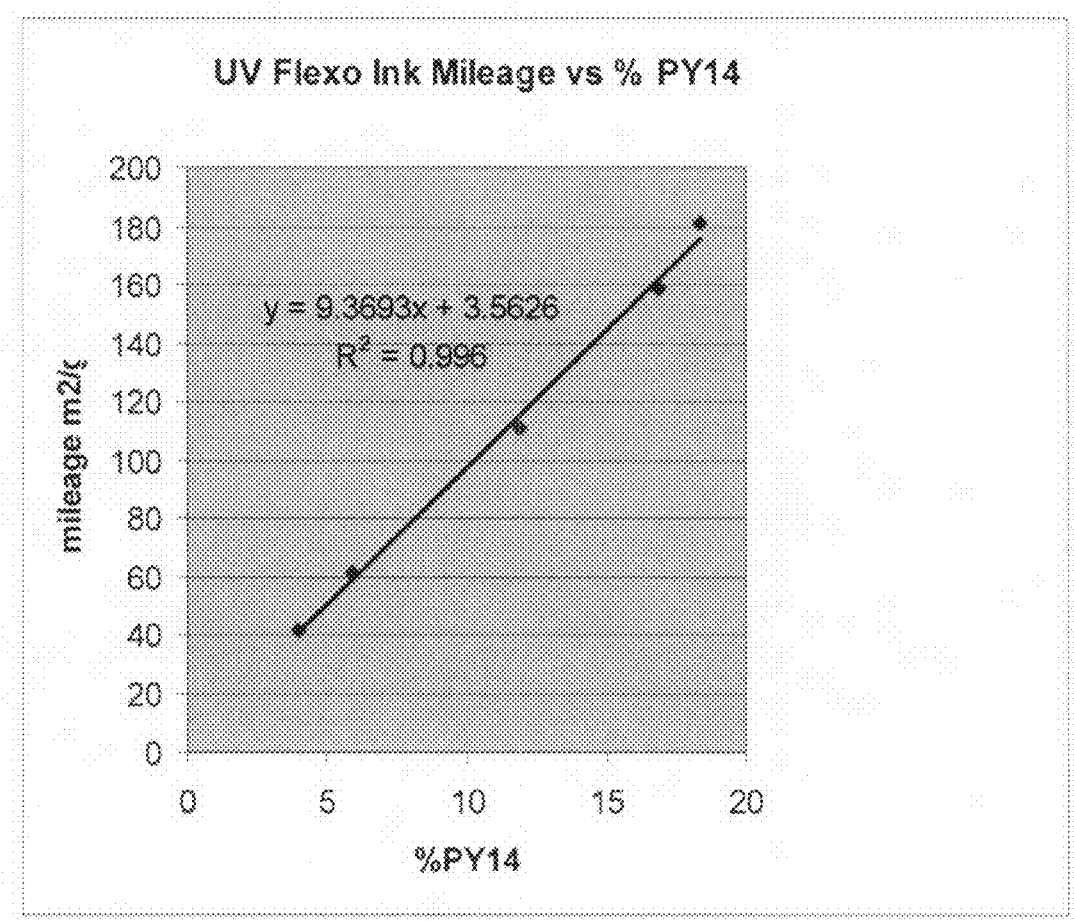
FIG. 15 shows a chart of Mileage Vs % pigment in UV Flexo Yellow 14 inks.

Predicting Ink Mileage of Yellow UV Flexo Inks at Varying Pigment Concentrations The capability of the present invention method to accurately differentiate and predict ink mileage of yellow UV Flexo inks was illustrated by determining the ink mileage of five PY14 inks at varying pigment concentration ranging from 3.9% to 18.4% and at O.D. 0.977 to 1.076 as described previously in the Section entitled "Calculating Ink Mileage of Yellow Ink Prints". The plot of % pigment in the against the corresponding ink mileage shows a linear relationship with a correlation coefficient of 0.9960. See Table 17 and FIG. 15.

TABLE 17

Mileage of PY14 UV-Flexo inks

| % PY 14 in ink | Mileage $m^2$/g | O.D. |
|---|---|---|
| 3.94 | 41.2 | 0.998 |
| 5.95 | 61.1 | 1.076 |
| 11.94 | 111.1 | 0.977 |
| 16.89 | 158.6 | 1.006 |
| 18.38 | 180.8 | 1.009 |

EXAMPLE 7

Figure 16:
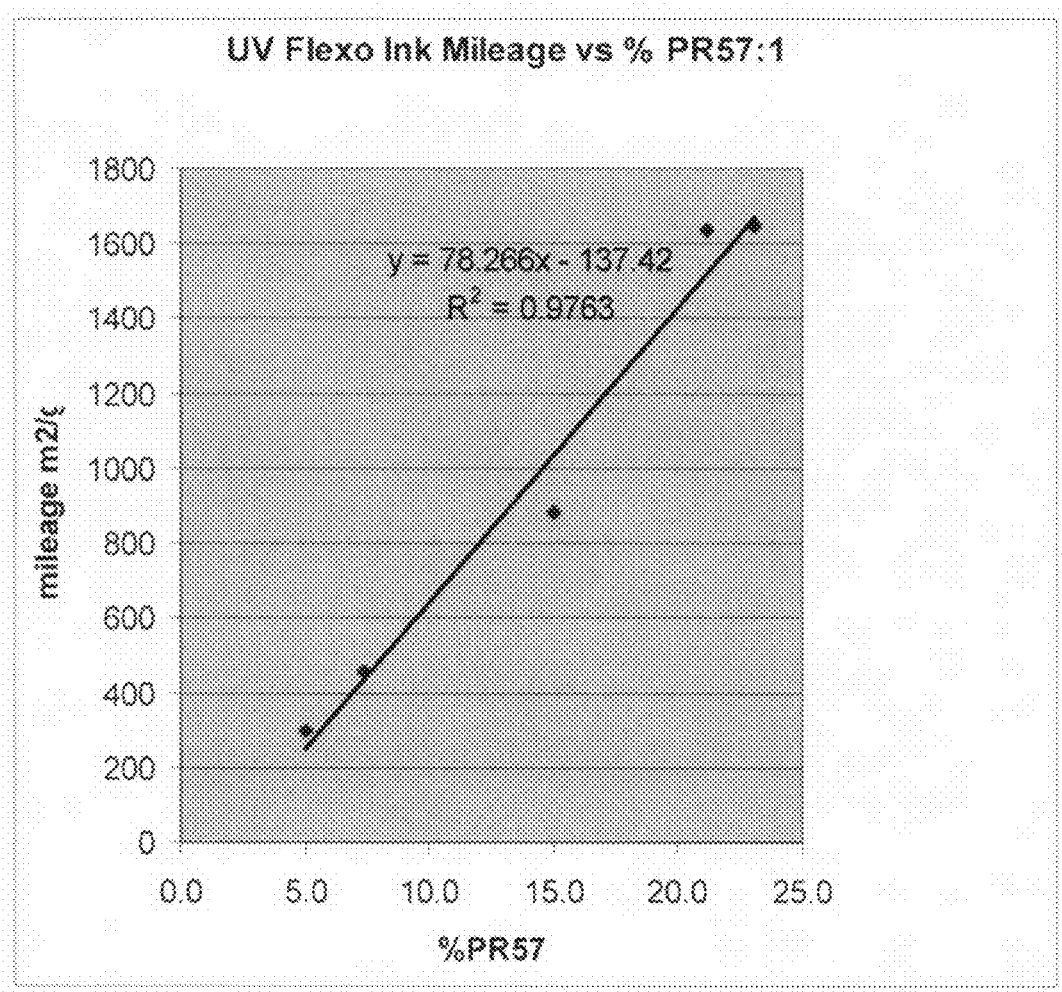
FIG. 16 shows a chart of Mileage Vs % pigment in UV Flexo PR57:1 inks.

Predicting Ink Mileage of Magenta UV Flexo Inks at Varying Pigment Concentrations The capability of this invention method to accurately differentiate and predict ink mileage of magenta UV Flexo inks was illustrated by determining the ink mileage of five PR57:1 inks at varying pigment concentration ranging from 5.0% to 23.1% and at O.D. 0.896 to 1.029 as described previously in the Section entitled "Calculating Ink Mileage of Magenta Ink Prints". The plot of % pigment in the against the corresponding ink mileage shows a linear relationship with a correlation coefficient of 0.9763. See Table 18 and FIG. 16.

TABLE 18

Mileage of PR57:1 UV-Flexo inks

| % PR57 in ink | Mileage $m^2$/g | O.D. |
|---|---|---|
| 5.0 | 299.7 | 0.896 |
| 7.4 | 453.2 | 1.028 |
| 15.0 | 885.2 | 1.000 |
| 21.2 | 1636.4 | 1.029 |
| 23.1 | 1650.1 | 0.997 |

EXAMPLE 8

Predicting Ink Mileage of Cyan UV Flexo Inks at Varying Pigment Concentrations

Figure 17:
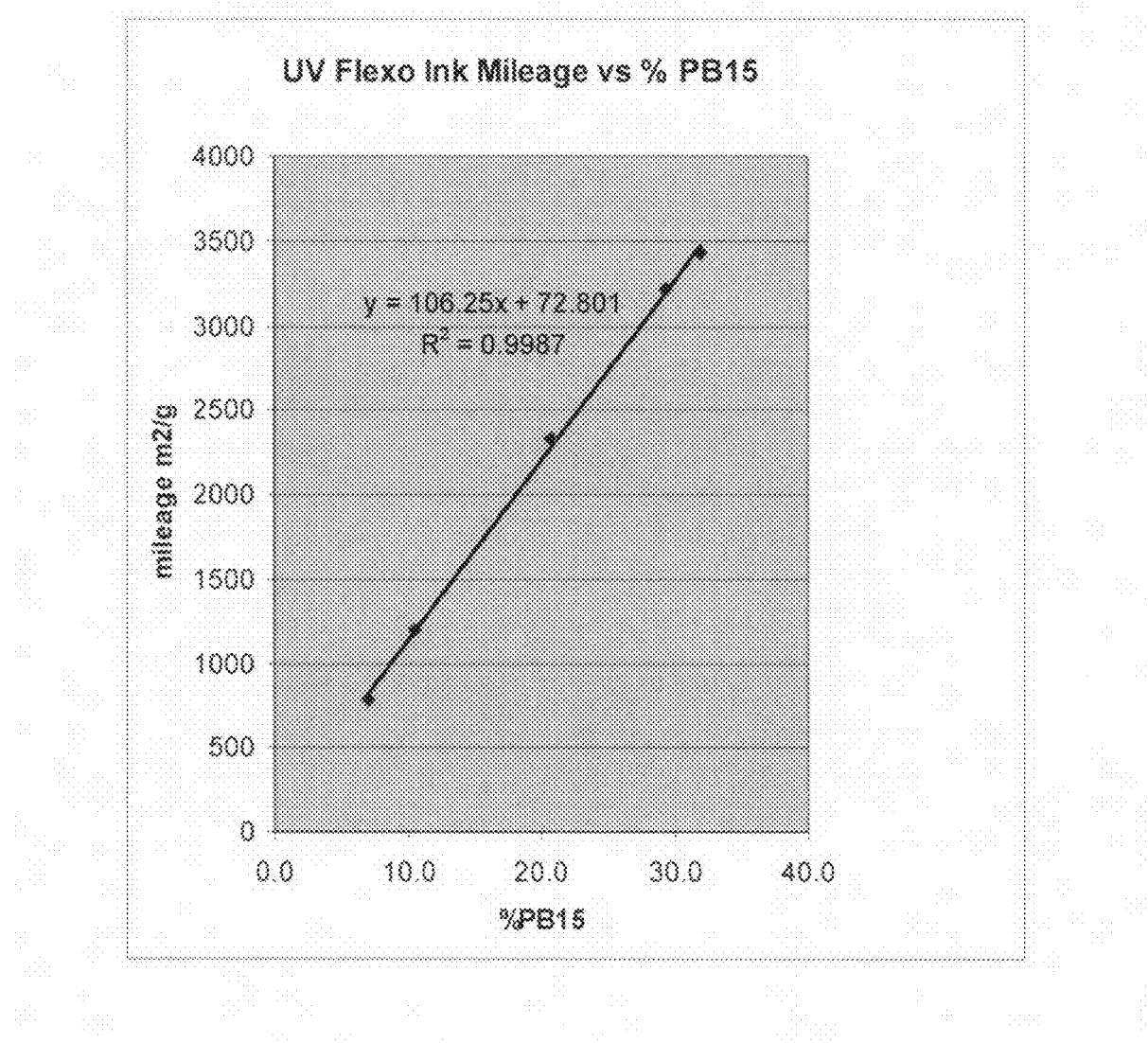
FIG. 17 shows a chart of Mileage Vs % pigment in UV Flexo PB15 inks.

The capability of the present invention method to accurately differentiate and predict ink mileage of cyan UV Flexo inks was illustrated by determining the ink mileage of five PB 15 inks at varying pigment concentration ranging from 7.0% to 32.04% and at O.D. 0.959 to 1.183 as described previously in the Section entitled "Calculating Ink Mileage of Magenta Ink Prints". The plot of % pigment in the against the corresponding ink mileage shows a linear relationship with a correlation coefficient of 0.9987. See Table 19 and FIG. 17.

TABLE 19

Mileage of PB 15 UV-Flexo inks

| % PB15 in ink | Mileage $m^2$/g | O.D. |
|---|---|---|
| 7.0 | 781.6 | 0.959 |
| 10.5 | 1197.2 | 1.114 |
| 20.7 | 2328.9 | 1.183 |

TABLE 19-continued

Mileage of PB 15 UV-Flexo inks

| % PB15 in ink | Mileage m²/g | O.D. |
|---|---|---|
| 29.4 | 3212.7 | 1.053 |
| 32.0 | 3425.8 | 1.011 |

The invention has been described in terms of preferred embodiments thereof, but is more broadly applicable as will be understood by those skilled in the art. The scope of the invention is only limited by the following claims.

What is claimed is:

1. A method for determining printing ink usage efficiency in a printing process based on an analysis of a pigment in a printed ink, said method comprising:
   (a) extracting said printed ink containing said pigment from a printed surface area into a liquid solution;
   (b) measuring amount of said pigment in the extracted ink; and
   (c) calculating said printing ink usage efficiency based on the analysis of and the amount of pigment in said area.

2. The method of claim 1, wherein the pigment absorbs UV-Visible light.

3. The method of claim 1, wherein said pigment is selected from the group consisting of azo and phthalocyanine pigments.

4. The method of claim 2, wherein the measurement of the amount of said pigment in extracted ink comprises:
   (a) placing said liquid solution in a container transparent to UV-Visible light;
   (b) measuring absorbance amount of said pigment in extracted ink by UV-Visible spectrophotometry at a specific wavelength; and
   (c) calculating concentration of said pigment using the following equation:

$c = A/a_{80}b$ where A is the measured absorbance, $a_{80}$ is an absorptivity coefficient of said pigment and is dependent on said wavelength, b is the path length of said container, and c is the pigment concentration is said liquid solution; and
   (d) calculating absolute amount of said pigment in said liquid solution.

5. The method of claim 1, wherein said ink is selected from the group consisting of publication inks and packaging inks.

6. The method of claim 5, wherein said ink is selected from the group consisting of gravure inks, flexo inks and offset inks.

7. The method of claim 1, wherein said printed surface area contains a color bar or registration mark.

8. The method of claim 1, wherein said printed surface area is from about 2 mm² to about 1575 mm².

9. The method of claim 1, wherein said printing ink usage efficiency is expressed in m²/kg of printing ink.

10. The method of claim 1, wherein said liquid ink solution is filtered prior to step (b).

11. The method of claim 1, wherein Optical Density is measured for said printed area prior to the extraction of step (a).

12. The method of claim 11, wherein said ink usage efficiency is expressed as ink usage efficiency at a measured Optical Density.

13. The method of claim 1 further comprising measuring the reflectance color saturation for said printed area prior to the extraction of step (a).

14. The method of claim 4, wherein said absorptivity coefficient $a_{80}$ is expressed as Liters $mg^{-1}$ $cm^{-1}$.

15. The method of claim 14, wherein said pigment concentration c is expressed in mg/Liter.

16. The method of claim 1, wherein the liquid solution used to extract said printing ink is selected from the group consisting of ortho-dichlorobenzene, 1-methylnaphthalene and acidified aqueous ethanol.

17. The method of claim 1, wherein said liquid solution used to extract said printing ink is ortho-dichlorobenzene and said pigment is an azo yellow pigment.

18. The method of claim 1, wherein said liquid solution used to extract said printing ink is 1-methylnaphthalene and said pigment is phthalocyanine pigment.

19. The method of claim 1, wherein said liquid solution used to extract said printing ink is an acidified aqueous ethanol and said pigment is an azo magenta pigment.

20. A method for determining ink usage efficiency at a desired Optical Density or a SWOP density comprising:
   (a) determining ink usage efficiency at measured Optical Density according to claim 12; and
   (b) determining ink usage efficiency at SWOP density according to the following formula:

ink usage efficiency at SWOP density=(ink usage efficiency at measured Optical Density).(C.F.), wherein C.F. is a correction factor to adjust for variation in pigment saturation within a given SWOP Optical Density range.

* * * * *